(12) United States Patent
Ching et al.

(10) Patent No.: US 6,534,320 B2
(45) Date of Patent: *Mar. 18, 2003

(54) PROCESS FOR IMMUNOCHROMATOGRAPHY WITH COLLOIDAL PARTICLES

(75) Inventors: Shanfun Ching, Libertyville, IL (US); Patricia A. Billing, Gurnee, IL (US); Julian Gordon, Lake Bluff, IL (US)

(73) Assignee: Abbott Laboratories, Abbott Park, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/046,171

(22) Filed: Mar. 23, 1998

(65) Prior Publication Data

US 2001/0006821 A1 Jul. 5, 2001

Related U.S. Application Data

(63) Continuation of application No. 08/543,227, filed on Oct. 13, 1995, now abandoned, which is a continuation of application No. 08/260,612, filed on Jun. 16, 1994, which is a continuation of application No. 07/809,598, filed on Dec. 18, 1991, which is a continuation of application No. 07/072,459, filed on Jul. 13, 1987, now Pat. No. 5,120,643.

(51) Int. Cl.$^7$ ............................................. G01N 33/559
(52) U.S. Cl. ....................... 436/514; 436/506; 436/518; 436/524; 436/525; 435/7.92; 435/5

(58) Field of Search ................................. 436/514, 506, 436/518, 524, 525; 435/5, 7.92

(56) References Cited

U.S. PATENT DOCUMENTS

| 4,022,876 A | | 5/1977 | Anbar | 424/1 |
| 4,092,116 A | * | 5/1978 | Giaever | 23/230 B |

(List continued on next page.)

FOREIGN PATENT DOCUMENTS

| EP | 0046004 | 2/1982 |
| EP | 0063810 | 11/1982 |

(List continued on next page.)

OTHER PUBLICATIONS

Chan, Daniel W. (Ed.), *Immuoassay, A Practical Guide*, Academic Press, pp. 40–42, (1987).

(List continued on next page.)

*Primary Examiner*—Lynette R. F. Smith
*Assistant Examiner*—Ginny Allen Portner
(74) *Attorney, Agent, or Firm*—Regina M. Anderson

(57) ABSTRACT

The present invention relates to improved specific binding assay methods, kits and devices utilizing chromatographically mobile specific binding reagents labelled with colloidal particles. Specific binding reagents labelled with colloidal particles such as gold and selenium may be subjected to rapid chromatographic solvent transport on chromatographic media by means of selected solvents and chromatographic transport facilitating agents. Further, impregnation of solid substrate materials with labile protein materials including colloidal particle and enzyme labelled reagents in the presence of meta-soluble proteins provides for the rapid resolubilization of such materials which have been dried onto such substrate materials.

13 Claims, 3 Drawing Sheets

U.S. PATENT DOCUMENTS

| | | | |
|---|---|---|---|
| 4,094,647 A | 6/1978 | Deutsch et al. ......... | 23/253 TP |
| 4,122,030 A | 10/1978 | Smith et al. ............ | 252/313 R |
| 4,166,105 A | 8/1979 | Hirschfeld .................. | 424/8 |
| 4,168,146 A | 9/1979 | Grubb et al. ............. | 23/230 B |
| 4,200,690 A * | 4/1980 | Root et al. ..................... | 435/7 |
| 4,235,601 A | 11/1980 | Deutsch et al. ........... | 23/230 B |
| 4,313,734 A | 2/1982 | Leuvering ................. | 23/230 B |
| 4,361,537 A | 11/1982 | Deutsch et al. .............. | 422/56 |
| 4,373,932 A | 2/1983 | Gribnau et al. ............. | 436/501 |
| 4,407,943 A | 10/1983 | Cole et al. ..................... | 435/7 |
| 4,452,901 A | 6/1984 | Gordon et al. .............. | 436/506 |
| 4,517,288 A | 5/1985 | Giegel et al. .................. | 435/7 |
| 4,703,017 A | 10/1987 | Campbell et al. ........... | 436/501 |
| 4,740,468 A | 4/1988 | Weng et al. .................... | 435/7 |
| 4,748,042 A * | 5/1988 | Linnecke et al. .............. | 427/2 |
| 4,775,636 A | 10/1988 | Moeremans et al. ........ | 436/518 |
| 4,818,686 A * | 4/1989 | Kortright et al. .............. | 435/7 |
| 4,843,019 A * | 6/1989 | Escribano-Crespo et al. .......................... | 436/501 |
| 4,855,240 A | 8/1989 | Rosenstein et al. ......... | 436/514 |
| 4,859,604 A * | 8/1989 | Gould et al. .................. | 436/15 |
| 4,861,711 A * | 8/1989 | Friesen .......................... | 436/7 |
| 4,879,215 A | 11/1989 | Weng et al. .................... | 435/7 |
| 4,916,056 A | 4/1990 | Brown, III et al. ............. | 435/7 |
| 4,943,522 A | 7/1990 | Eisinger et al. ................. | 435/7 |
| 4,954,452 A | 9/1990 | Yost et al. ................... | 436/524 |
| 4,960,691 A * | 10/1990 | Gordon et al. .................. | 435/6 |
| 4,960,692 A * | 10/1990 | Lentrichia et al. ............. | 435/7 |
| 4,962,023 A | 10/1990 | Todd et al. ..................... | 435/7 |
| 5,091,318 A * | 2/1992 | Anawis et al. .............. | 436/513 |
| 5,120,643 A | 6/1992 | Ching et al. ............... | 435/7.92 |
| 5,141,850 A | 8/1992 | Cole et al. ................... | 435/525 |
| 5,266,497 A | 11/1993 | Imai et al. ................... | 436/514 |
| 5,281,522 A * | 1/1994 | Senyei et al. ................. | 435/7.9 |
| 5,310,647 A * | 5/1994 | Kerschensteiner ............. | 435/4 |
| 5,310,650 A * | 5/1994 | McMahon et al. .............. | 435/6 |
| 5,578,577 A * | 11/1996 | Ching et al. ................... | 514/21 |
| 5,599,668 A * | 2/1997 | Stimpson et al. .............. | 435/5 |
| 5,641,689 A * | 6/1997 | Van Doorn et al. ......... | 436/524 |
| 5,670,381 A * | 9/1997 | Jou et al. ..................... | 436/518 |
| 5,712,172 A * | 1/1998 | Huang ......................... | 436/518 |
| 5,976,527 A * | 11/1999 | Siol ........................... | 424/94.1 |

FOREIGN PATENT DOCUMENTS

| | | | | |
|---|---|---|---|---|
| EP | 0 135 324 A2 | 3/1985 | .......... | G01N/33/53 |
| EP | 0158746 A2 | 10/1985 | | |
| EP | 0 164 194 B1 | 12/1985 | .......... | G01N/30/92 |
| EP | 0 191 640 A2 | 6/1986 | .......... | G01N/33/52 |
| EP | 192320 A1 | 8/1986 | | |
| EP | 0250137 | 12/1987 | | |
| EP | 284232 A1 | 9/1988 | | |
| EP | 0298368 | 1/1989 | | |
| EP | 0 207 152 B1 | 12/1992 | .......... | G01N/33/53 |
| EP | 0 225 054 B1 | 1/1993 | .......... | G01N/33/52 |
| WO | 86/04095 | 7/1986 | | |
| WO | 88/08534 | 11/1988 | | |
| WO | 9303175 | * 2/1993 | | |

OTHER PUBLICATIONS

Gershoni, Jonathan, et al., "Electrophoretic Transfer of Proteins from Sodium Dodecyl Sulfate–Polyacrylamide Gels to a Positively Charged Membrane Filter", *Analytical Biochemistry*, 124:396–405, (1982).

Gribnau, T.C.J., et al., "Particle–labelled Immunoassays: A Review", *Journal of Chromatography*, 376:175–189, (1986).

Hunter, R.J., *Foundation of Colloid Science*, Clarendon Press, Oxford, 1:1–4, (1987).

Maggio, Edward T., *Enzyme Immunoassay*, CRC Press, Inc., pp. 175–176 and 194, (1980).

De Mey, J., "Colloidal Gold Probes in Immunocytochemistry", *Immunocytochemistry: Applications in Pathology and Biology*, Polakm van Noorden (Eds), Wright & Sons, Ltd., pp. 82–112, (1983).

O'Connell, James, P., et al., "A Highly Sensitive Immunoassay System involving Antibody–Coated Tubes and Liposome–Entrapped Dye", *Clin. Chem.* 31(9):1424–1426, (1985).

Rosmalen, F.M.A., et al., "A sensitive radioimmunoassay of atrial natriuretic peptide in human plasma, using a tracer with an immobilized glycouril agent", *Clinical Chimica Acta.*, 165:331–340, (1987).

Saunders, George, C., "The Art of Solid–Phase enzyme Immunoassay Including Selected Protocols", *Immunoassays in the Clinical Laboratory*, pp. 99–118, (1979).

Tijssen, P., "Practice and Theory of Enzyme Immunoassays", *Laboratory Techniques in Biochemistry and Molecular Biology*, 15:297–333, (1985).

Uotila, Marjatta, et al., "Two–Site Sandwich Enzyme Immunoassay with Monoclonal Antibodies to Human Alpha–Fetoprotein," *Journal of Immunological Methods*, 42:11–15, (1981).

Kenna et al., Journal Immunol. Methods, 85, 409–419 (1985).

Vogt et al., Journal Immunol. Methods, 101, 43–50 (1987).

Romano et al., Immunochemistry, 11, 521–522 (1974).

Frens, Nature Physical Science, 241, Jan. 1, 1973.

Surek et al., Biochemical and Biophysical Research Communication, 121, (1984).

Geoghegan et al., Journal of Immunological Methods, 34 11–21 (1980).

Hsu et al., Analytical Biochemistry, 142, 221–225 (1984).

* cited by examiner

FIG. 1a
FIG. 1b
FIG. 1c
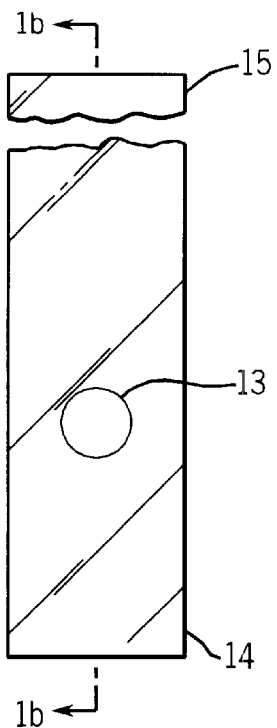
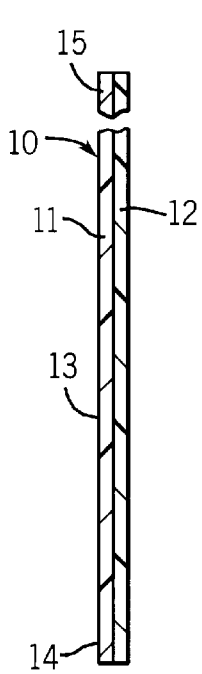
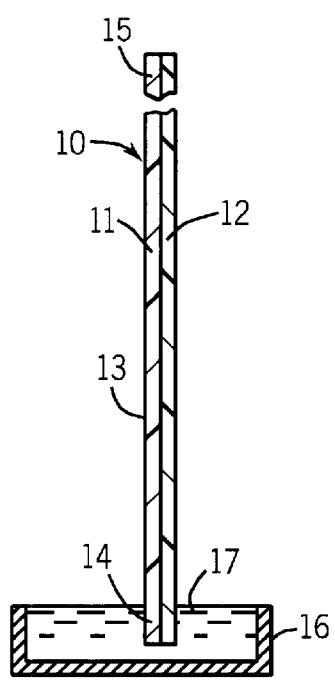
FIG. 2a
FIG. 2b
FIG. 2c
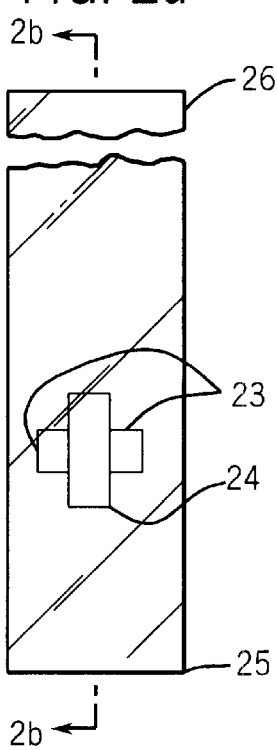
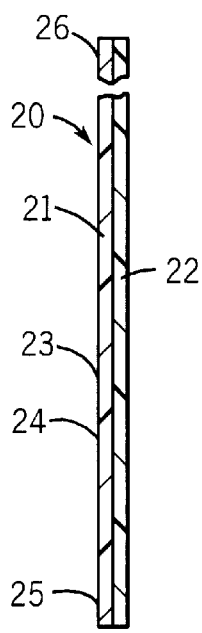
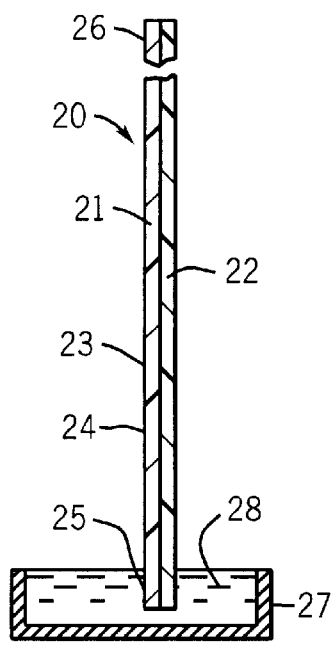

PROCESS FOR IMMUNOCHROMATOGRAPHY WITH COLLOIDAL PARTICLES

The present application is a continuation of U.S. Ser. No. 08/543,227, filed on Oct. 13, 1995, now abandoned which is a continuation of U.S. Ser. No. 08/260,612, filed on Jun. 16, 1994, which is a continuation of U.S. Ser. No. 07/809,598, filed on Dec. 18, 1991, which is a continuation of U.S. Ser. No. 07/072,459, filed on Jul. 13, 1987, now U.S. Pat. No. 5,120,643.

BACKGROUND

The present invention relates generally to assay devices and specifically to those devices making use of chromatographic techniques in conducting specific binding assays. According to one aspect of the invention, methods and devices are provided utilizing colloidal particle labelled specific binding materials which are chromatographically mobile and capable of producing visually detectable signals. According to another aspect of the invention, methods and devices are provided utilizing labelled specific binding materials including colloidal particle labelled materials and enzyme labelled materials which are dried onto a chromatographic medium in the presence of a meta-soluble protein and are capable of being rapidly resolubilized in the presence of an appropriate solvent such as the sample or a chromatographic transport solvent.

Immunological assays have proven to be of great value in a variety of clinical applications. Such assays depend upon specific binding reactions between immunoglobulins (antibodies) and materials presenting specific antigenic determinants (antigens). Antibodies bind selectively with ligand materials presenting the antigen for which they are specifically reactive and are capable of distinguishing the ligand from other materials having similar characteristics.

Because the results of immunological and other specific binding reactions are frequently not directly observable, various techniques have been devised for their indirect observation. Such techniques involve labelling of one of the members of the specific binding pair with a radioisotope, chromophore, fluorophore or enzyme label. Radiolabels, chromophores and fluorophores may be detected by the use of radiation detectors, spectrophotometers or the naked eye. Where members of a specific binding pair are tagged with an enzyme label, their presence may be detected by the enzymatic activation of a reaction system wherein a compound such as a dyestuff, is activated to produce a detectable signal.

There are three well known types of immunological specific binding assays. In competitive binding assays, labelled reagents and unlabelled analyte compounds compete for binding sites on a binding material. After an incubation period, unbound materials are washed off and the amount of labelled reagent bound to the site is compared to reference amounts for a determination of the analyte concentration in the sample solution. A second type of immunological assay is known as a sandwich assay and generally involves contacting an analyte sample solution to a surface presenting a first binding material immunologically specific for that analyte. After a wash step, a solution comprising a labelled second binding material specifically reactive with the analyte to be detected is then added to the assay. The labelled second binding material will bind to any analyte which is itself bound to the first binding material. The assay system is then subjected to a wash step to remove any labelled second binding material which failed to bind with the analyte. The amount of labelled material remaining may then be determined and will be indicative of the amount of analyte present in the sample. While the term sandwich assay is frequently understood to relate to immunological assays wherein the first and the labelled reagent materials are both antibodies or are both antigens such that the "sandwich" is of the form antibody/antigen/labelled antibody, a broader definition of the term sandwich-type assay is understood as including other types of three component assays including what are sometimes referred to as "indirect sandwiches", which may be of the form antigen/antibody/labelled (anti-immunoglobulin) antibody.

A third type of immunological assay is the agglutination assay which is exemplified by well-known assays for blood antigens and serum types. Immunological reactivity between antibodies within serum and antigens presented on red blood cell surfaces is indicated by the formation of a three dimensional cross-linked network of antigen (red blood cells) and antibodies. The agglutination of the serum/red blood cell mixture results in the formation of a macroscopic pellet in the testing well which can be visible to the naked eye.

These various immunoassay procedures were originally performed as "liquid phase" assays in apparatus such as test tubes where antigen/antibody conjugates were centrifuged and precipitated. More recently, methods have been developed wherein antibodies or antigens are coated onto the surface of microtiter wells and reactions are carried out in solution in such wells. Methods have also been developed for carrying out "solid phase" assays wherein immunological reactions are carried out in solution on solid substrates including those which are porous or fibrous materials. According to such procedures, porous carrier materials are fashioned into strips or other forms to which antibodies or antigens are immobilized by adsorption, absorption or covalent bonding. Sample materials containing an analyte specifically reactive with the immobilized member of the binding pair are applied to the carrier material where the analyte is immobilized by reaction with its corresponding binding pair member. The non-reacted sample materials are then removed by a washing step after which, in the case of a sandwich-type assay, a labelled reagent is applied to the carrier material which is capable of reaction with and immobilization by the immobilized analyte. The carrier material is then washed in order that the presence of the labelled reagent, and hence the analyte, may be detected.

Modifications of such "solid phase" assays are known wherein one or more of the sample components or reagents is moved by means of chromatographic solvent transport. U.S. Pat. No. 4,168,146 to Grubb, et al., discloses porous test strips to which antibodies have been immobilized. The strips are then contacted with measured amounts of aqueous solution containing the analyte antigen. Antigen molecules within the test solution migrate by capillary action throughout the test strip, but because the bound antibodies retard the migration of the antigens for which they are specific, the extent of migration of the antigen molecules over a fixed time period is a function of the antigen concentration in the test solution. The antigen-containing areas of the diagnostic device are then indicated by the addition of enzyme or fluorescent chromophore labelled antibodies.

U.S. Pat. No. 4,517,288 to Giegel, et al. discloses methods for conducting solid phase immunoassays on inert porous materials. The patent discloses immunologically immobilizing a binding material within a specified zone of the porous material and applying the sample to the zone containing the immobilized binding material. An enzyme labelled indicator material which will bind with the analyte is then applied to the zone where it will become immobilized in an amount correlated to the amount of analyte in the zone. A solvent is then applied to the center of the zone to chromatographically remove the unbound labelled indicator from the zone so that the amount of labelled indicator remaining in the zone may be measured.

Of interest to the present invention are the disclosures of the Deutsch, et al., U.S. Pat. Nos. 4,094,647, 4,235,601 and 4,361,537 which relate to immunological and other types of specific binding assays wherein reagents are transported by chromatographic solvent transport. According to one embodiment, a radiolabelled competitive binding assay kit comprises a strip capable of transporting a developing liquid by capillarity having a first zone for receiving a sample, a second zone impregnated with a first reagent capable of being transported by the developing liquid and a third zone impregnated with a second reagent. In addition, the devices comprise a measuring zone and a retarding element which may be either the second reagent or the material of the strip. The first reagent is capable of reacting with one of the group consisting of (1) the sample, (2) the sample and the second reagent, or (3) the second reagent in competition with the sample, to form a product in an amount dependent on the characteristic being determined. A sample is contacted with the first zone and the strip is then dipped into the developing liquid to bring about transport of the sample and the first reagent to form the reaction product. The retarding element slows transport of either the product or the first reagent (the moving reagent) to spacially separate the two and the amount of the moving element is then measured at the measurement location.

The Deutsch, et al., patents relate to methods wherein reagents located on the chromatographic material are mixed with the sample material and other reagents during the course of chromatographic transport. Such mixing is not detrimental to and may even be desirable for competitive binding assays. It may, however, be undesirable for sandwich-type binding assays where it is necessary to prevent contact between non-analyte sample materials and labelled specific binding reagents.

Of interest to the present invention is the disclosure of U.S. Pat. No. 4,452,901 to Gordon which relates to the use of porous nitrocellulose supports for immobilization of proteins. It is disclosed that such nitrocellulose sheets may be utilized in immunoassay procedures if the residual binding capacities of the nitrocellulose sheets are saturated by blocking treatment with one or more types of proteins, different from those immobilized and not cross-reactive with any of the antibodies subsequently used in the assay.

Of further interest to the background of the invention are the disclosures of Gordon, EPO Application 63,810, published Nov. 3, 1982, relating to devices for conducting immunological assays. The devices consist of a porous solid support containing a preselected array of delimited adsorption areas of antigens, antibodies or both, wherein residual adsorption sites on the substrate are saturated by protein blocking agents such as bovine serum albumin. Porous solid supports are selected from a variety of natural and synthetic polymers and derivatives but are preferably nitrocellulose sheets 0.1 mm thick with pore size between about 0.15 $\mu$m and about 15 $\mu$m. Antigens or antibodies are applied to the porous solid support by direct contact followed by incubation with blocking agents. Assays for detection of unknown antigens or antibodies are then carried out through use of labelled antibodies which may also be anti-immunoglobulin antibodies.

Also of particular interest to the present application is the disclosure of co-owned U.S. Pat. No. 4,960,691, filed Sep. 29, 1986 by Gordon, et al., which is hereby incorporated by reference and which relates to devices for conducting specific binding assays utilizing the sequential chromatographic transport of analyte and reagent materials. Wash and addition steps are inherently carried out and liquid "microcircuitry" can be programmed to carry out a variety of multistep procedures and to avoid the premature mixing of sample materials and reagents. Preferred blocking solutions for treatment of the strip materials include include 1% LB gelatin (Inotech, Wohlen, Switzerland) in TBS solution comprising (0.15 M NaCl, 0.02 Tris-HCl, pH 7.6) or 3% bovine serum albumin (BSA) solution in physiological saline.

Specifically, the Gordon, et al., sequential transport application relates to devices which comprise a test strip for the detection of an analyte in a sample comprising a length of chromatographic material having the capacity for rapid chromatographic solvent transport of non-immobilized reagents and reactive sample components by means of a selected chromatographic solvent. The strip includes a first end at which chromatographic transport begins, a second end at which chromatographic transport ends and a plurality of zones positioned between the two ends. The zones include a first zone (impregnated with a first reagent which is mobile in the solvent and capable of reaction with, and immobilization against solvent transport by the analyte when the analyte is in immobilized form), a second zone (for receiving the sample suspected of containing an analyte) and a third zone (positioned downstream of the first zone and impregnated with a second reagent which is immobilized against solvent transport and is capable of selective reaction with the analyte so as to render the analyte in an immobilized form in the third zone). The device is further characterized in that after the sample is received in the second zone and upon the first end being dipped into the chromatographic solvent, the relative mobility of the analyte and the first reagent or the site relationship between the second and third zones is such that the analyte is disposed and immobilized against solvent transport at the third zone prior to the first reagent reaching the third zone, whereby interfering sample components and non-analyte components of the sample which are reactive with the first reagent are cleared from the third zone by chromatographic solvent transport prior to transport of the first reagent to the third zone. The presence of the first reagent immobilized at the third zone may be detected by means of enzyme, radioisotope or other labels. The device is particularly suited for use with enzyme labelled reagents as enzyme substrates and indicator dye reagents may be incorporated on separate zones on the strip and transported to the third zone in an appropriate sequence by chromatographic transport.

Of interest to the present invention are those references relating to the use of dispersions of colloidal particles in immunological assay procedures. Frens, Nature, 241, 20–23 (1973) discloses methods for the preparation of monodisperse gold sols of various particle sizes through the reduction of gold chloride with aqueous sodium citrate. Variation in the concentration of sodium citrate during the nucleation of the particles may be used to vary the particle size of the resulting sols. Sols of mono-dispersed gold particles are disclosed having particle sizes ranging from 16 nm to about 150 nm and exhibiting colors ranging from orange to red to violet over that range.

Romano, et al., Immunochemistry, 11, 521–22 (1974) discloses the labeling of immunoglobulins with colloidal gold particles for use in imaging human red blood cell antigens by means of electron microscopy. The gold sol, which has an average particle diameter of about 3 nm, has a tendency to flocculate but is stabilized by the presence of either horse serum or BSA.

Geoghegan, et al., J. Immuno. Meth., 34, 11–21 (1980) discloses the coating of colloidal gold particles with immunoglobulins for use in passive agglutination procedures. The reference (at page 14) discloses the resuspension of centrifuged pools of gold labelled immunoglobulins with 0.01 M phosphate buffered saline (PBS) (pH 7.2) containing 1% polyethylene glycol (PEG). The reference also notes that while the gold-protein complexes do not aggregate during centrifugation, they are often subject to non-specific aggregation in the presence of any serially diluted protein in a microtiter plate.

Surek, et al., Biochem. and Biophys. Res. Comm., 121, 284–289 (1984) discloses the use of protein A labelled colloidal gold particles for the detection of specific antigens immobilized on nitrocellulose membranes. According to the procedure, an electrophoresis gel is blotted onto a nitrocellulose filter which is then treated with a 2% solution of BSA in PBS to prevent non-specific binding. The filter is treated with diluted antiserum or preimmune serum and washed with PBS-BSA. The strip is then incubated for 30 to 60 minutes with protein A conjugated with colloidal gold which detects the presence of bound antibodies. Excess unbound colloidal gold particles are then removed by several short buffer washes.

Leuvering, U.S. Pat. No. 4,313,734 discloses the use of metal sol particles as labels for in vitro determination of immunological components in an aqueous test medium. Specifically disclosed are immunoassay test kits for the detection of antigens or antibodies employing one or more labelled components obtained by coupling the component to particles of an aqueous sol dispersion of a metal, metal compound or polymer nuclei coated with a metal or metal compound having a particle size of at least 5 nm. According to one example, an assay for human placental lactogen (HPL) is conducted with the use of rabbit anti-HPL antibodies which have been labelled with gold particles. Unlabelled rabbit anti-HPL antibodies are coated onto the walls of microtiter plate wells by incubation with BSA solution and phosphate buffer to which merthiolate has been added. Standard solutions of HPL are added to the wells and were incubated for 2 hours at room temperature. A solution consisting of rabbit anti-HPL antibodies which has been conjugated with gold particles having diameters between 45 and 70 nm is added to the wells and incubated at room temperature overnight. The wells are then washed and light absorption measured with a small-volume spectrophotometer.

Hsu, Anal. Biochem. 142, 221–225 (1984) discloses the use of immunogold marker systems for blot immunoassay procedures wherein serial dilutions of purified tobacco mosaic virus (TMV) are electrophoresed in a polyacrylamide gel and are then electrotransferred to nitrocellulose filter sheets. The nitrocellulose sheets are baked to stabilize binding and treated with 5% normal goat serum or in 0.05% TWEEN 20 (polyoxyethylene sorbitanmonolaurate) in PBS to block nonspecific antibody binding. The filter is incubated overnight at 4° C. with rabbit anti-TMV antibodies diluted in blocking solution followed by washing in PBS and the antigen-antibody complex is then detected by soaking the filter in gold-labelled goat anti-rabbit IgG in blocking solution. According to the procedure as little as 8 ng of the TMV protein is detectable with about 30 minutes exposure to the gold-labelled IgG. The reference also discloses that agents such as polyethylene glycol, polyvinylpyrrolidone and bovine serum albumin can enhance the stability of gold markers. The use of TWEEN 20 (polyoxyethylefle sorbitanmonolaurate) to prevent nonspecific binding of protein on nitrocellulose is disclosed along with the observation that 0.05% TWEEN 20 (polyoxyethylene sorbitanmonolaurate) in PBS can be used in the staining procedure without disturbing the specificity of the gold-IgG complexes. Normal goat serum is identified as a preferred blocking agent in light of its tendency to adsorb gold particles that may dissociate from the probe during storage.

Moeremans, et al., EPO Application No. 158,746 discloses the use of colloidal metal particles as labels in sandwich blot overlay assays. Specific binding materials specifically reactive with the analyte to be detected are applied to nitrocellulose strips and dried. Protein binding sites on the strip are then blocked by means of treatment with bovine serum albumin, gelatin, polyethylene glycol or polyoxyethylene sorbitanmonolaurate (TWEEN 20). Analyte containing sample material is then applied to the strip and incubated for 2 hours. The treated strip is washed and air-dried and incubated for 2 hours with a specific binding agent which has been labelled with colloidal metal particles. According to one example, anti-tubulin antibodies are detected by gold particle labelled reagents producing a pink-reddish color (20 nm particles) or a purplish color (40 nm particles). The assays are disclosed to have a sensitivity on the order of 5 ng/$\mu$l.

Of interest to the present invention is the disclosure of Hoye J. Chromatog., 28, 379–384 (1967) relating to chromatographic purification of radiochemicals. The application of paper chromatography, thin layer chromatography and high voltage electrophoresis techniques are disclosed to move gold ions with varying degrees of success but are generally unsuitable for transporting colloidal gold particles.

The use of polymerized dye materials in colloidal form for specific binding assays is also known. Of interest to the present application is the disclosure of Hirschfeld, U.S. Pat. No. 4,166,105 which relates to labelled specific binding reagents reactive with specific antigens prepared by linking fluorescent dye molecules to analyte specific antibodies through polymers comprising reactive functional groups. Also of interest to the present application is the disclosure of Henry, U.S. Pat. No. 4,452,886 which relates to specific binding reagents comprising antigens or antibodies linked to a water-soluble polymer consisting essentially of between 40 and 600 chromophoric or fluorescent group containing monomers.

SUMMARY OF THE INVENTION

The present invention provides improved specific binding assay methods, kits and devices utilizing chromatographically mobile labelled materials. According to one aspect of the invention, methods and devices are provided utilizing colloidal particle labelled specific binding materials which are chromatographically mobile and capable of producing visually detectable signals. According to another aspect of the invention, methods and devices are provided utilizing labelled specific binding materials including colloidal particle labelled materials and enzyme labelled materials which are dried onto a chromatographic medium in the presence of a meta-soluble protein and are capable of being rapidly resolubilized in the presence of an appropriate solvent such as the sample or a chromatographic transport solvent.

It has been discovered that specific binding materials labelled with colloidal particles such as gold may be subjected to rapid chromatographic transport on a chromatographic medium by means of selected solvents and chromatographic transport facilitating agents and that use of chromatographic solvent transport assay techniques significantly reduces the time required for the binding reaction of a colloidal particle labelled material with its specific binding partner as compared with conventional methods. It has also been discovered that impregnation of solid substrate materials with labile proteins including labelled and unlabelled materials in the presence of an aqueous medium containing meta-soluble proteins such as casein allows the rapid resolubilization of such proteins which have been dried onto such substrate materials. Such resolubilized labelled materials may then be maintained in a liquid solution for carrying out liquid phase assays or electron microscopy. The drying of labile proteins in the presence of meta-soluble proteins thus provides an inexpensive means of storing such proteins, including colloidal particle labelled reagents, in a stable and convenient form from which they might then be resolubilized and subjected to chromatographic solvent transport. Alternatively, where the solid substrate material is a chromatographic medium, the labile proteins may be solubilized and chromatographically transported to carry out specific binding assay procedures.

Accordingly, the invention provides improved specific binding assay devices, kits and methods for determining the presence or amount of a substance in a sample. The colloidal particle labelled assays provide a visually detectable signal and do not require the use of materials such as radioisotopes or enzyme labels with the attendant requirement for detection equipment or addition of enzyme conjugates and indicator dyes. Means for conducting both competitive binding and direct binding (sandwich-type) assays are provided by the invention. Preferred assay methods and kits are provided for determining the presence or amount of a substance in a sample whereby a colloidal particle labelled material and a chromatographic transport facilitating agent are mixed with the sample. A chromatographic medium comprising one or more reaction sites impregnated with one or more reagents useful for carrying out the assay is then contacted with the mixture of sample, colloidal particle labelled material and chromatographic transport facilitating agent in order to chromatographically transport the sample and labelled material along the chromatographic medium and carry out the desired assay.

The invention also provides assay methods and devices wherein labelled materials including colloidal particle labelled materials and enzyme labelled materials are impregnated and dried onto a reaction site on a chromatographic substrate material in the presence of meta-soluble proteins. The chromatographic mediums of the devices may comprise one or more additional reaction sites where chemical reactions per se need not take place but where additional materials may be deposited or immobilized or where analyte substance containing sample materials may be deposited. The chromatographic medium is contacted with a chromatographic solvent which solubilizes and transports along the medium the colloidal particle labelled specific binding material as well as the sample substance and other optional materials and reagents. The affinity of the immobilized specific binding reagent is such that it efficiently captures the labelled material in the flowing material such that the labelled binding component is accumulated in the zone. Where the labelled material is a colloidal particle labelled material, an important advantage is provided by the present invention in that the binding affinity of the immobilized reagent may be such that it is capable of capturing a labelled component in the flowing chromatographic stream in such a way that the labelled binding component is accumulated in the capture zone and is clearly discernable over the background stream of non-concentrated colloidal particle labelled material.

BRIEF DESCRIPTION OF THE DRAWINGS

FIGS. 1a, 2a, 3a, 4a and 5a are front plan views of five different forms of the test devices of the present invention;

FIGS. 1b, 2b, 3b, 4b and 5b are cross-sectional views of the test devices shown in FIGS. 1a, 2a, 3a, 4a and 5a, respectively, taken along lines 1b—1b, 2b—2b, 3b—3b, 4b—4b and 5b—5b;

FIGS. 1c, 2c and 3c are cross-sectional views of the test devices shown in FIGS. 1a, 2a and 3a, respectively, in contact with a volume of sample material and indicator solution;

DETAILED DESCRIPTION

Figure 3A:
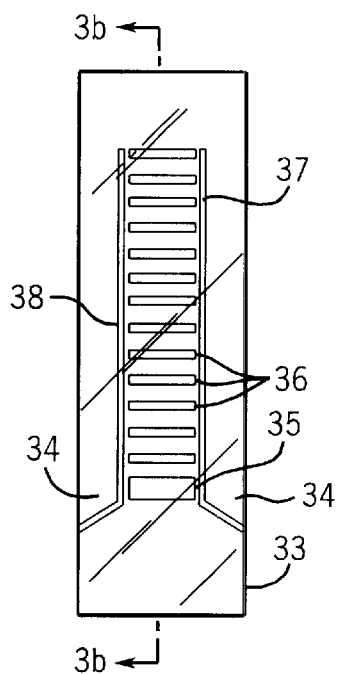

The present invention provides improved immunological and other specific binding assay methods, kits and devices utilizing chromatographically mobile labelled specific binding materials.

Colloidal particle labelled specific binding materials are highly susceptible to aggregation and are thus generally incapable of being rapidly and efficiently transported on chromatographic media according to chromatographic solvent transport assay methods. The invention is based on the discovery that specific binding materials labelled with colloidal particles, and particularly with colloidal particles larger than about 1 nm in diameter, which are especially subject to aggregation, may be subjected to rapid chromatographic transport on chromatographic media by means of selected solvents and chromatographic transport facilitating agents. While materials labelled with colloidal particles and particularly those less than about 1 nm in diameter may be capable of chromatographic transport without the presence of the chromatographic transport facilitating agents of the present invention, the use of such agents assists in the rapid chromatographic transport of all colloidal particle labelled reagents of the invention. As a related discovery, it has been found that chromatographic solvent transport of colloidal particle labelled materials significantly reduces the time required for the binding reaction of those materials with their specific binding partners as compared with conventional methods. While conventional immunoassay procedures such as those of Leuvering, U.S. Pat. No. 4,313,734 teach the incubation of colloidal particle labelled specific binding materials for from 1 hour to overnight (16 hours), the chromatographic methods of the present invention generally provide for the rapid completion of transport and specific binding reactions in less than about 5, and preferably less than about 2, minutes.

As another aspect of the present invention, it has furthermore been discovered that labile protein materials including colloidal particle, enzyme or other labelled materials which are impregnated and dried onto solid substrate materials in the presence of selected meta-soluble protein materials may be rapidly solubilized by means of suitable solvents. Where the solid substrate material is a chromatographic medium, the labelled materials may be rapidly resolubilized and transported along the chromatographic medium by means of selected chromatographic solvents. As a consequence of this discovery, specific binding assay devices are provided wherein labelled materials including colloidal particle labelled specific binding materials are incorporated in dry stable form on the device and only the sample material and a chromatographic solvent need be added for conducting an assay.

According to the invention, kits may be produced and specific binding assay methods may be practiced for analysis of a substance in a sample according to a method employing a solution comprising a colloidal particle labelled material. The method also employs a chromatographic medium having capillarity and the capacity for chromatographic solvent transport of non-immobilized reagents and reactive sample components by means of a selected chromatographic solvent including a reaction site including an immobilized reagent capable of binding a member selected from the group consisting of the substance to be analyzed and the colloidal particle labelled material. The method comprises (a) contacting the sample to be analyzed to the chromatographic medium, (b) chromatographically transporting on said chromatographic medium said colloidal particle labelled material whereby at least a portion of said colloidal particle labelled material is chromatographically transported to the reaction site for binding thereto, and (c) determining the detectable response produced by said colloidal material at the reaction site as an indication of the presence or amount of the substance in the sample.

According to preferred embodiments of the invention, the affinity of the immobilized reagent and the concentrations of reagents and sample materials may be selected by one of skill in the art such that the colloidal particle labelled material is accumulated at the reaction site and is detectable over the background stream of the non-concentrated colloidal particle labeled material. Where this is not the case, the chromatographic medium may be subjected to a wash or rinse step to remove the unbound labelled material. Such wash steps may also be inherently carried out according to the procedures of co-owned U.S. Pat. No. 4,960,691.

It is also to be understood that said sample to be analyzed, said colloidal particle labelled material, said chromatographic solvent and other solvents and reagents may be mixed with each other according to various possible combinations prior to their contacting the chromatographic medium and that these mixtures and various components may be contacted to the chromatographic medium in various sequences as would be apparent according to the skill in the art. It is to be further understood that the chromatographic solvent may be replaced by the sample or by the solution containing the colloidal particle labelled material where these materials are capable of transporting the colloidal particle labelled material to the reaction site at which the reagent is immobilized. It is also to be understood that the chromatographic solvent may inherently be used according to the methods of co-owned U.S. Pat. No. 4,960,691 to wash unreacted labelled materials and other non-immobilized sample components from the reaction site at which the reagent is immobilized. When the labelled material is contacted to the chromatographic medium at the reaction site at which the reagent is disposed, the chromatographic solvent transport may be used to accelerate the binding reaction between the colloidal particle labelled material and other specific binding reagents as well as wash non-immobilized labelled material from the zone.

A preferred embodiment of the invention is that wherein the indicator solution additionally comprises a chromatographic transport facilitating agent and it and the sample are mixed and contacted to the chromatographic medium to provide for chromatographic transport of the analyte substance and the labelled specific binding material. According to other embodiments, the sample material and the colloidal particle labelled material may be contacted to one or more reaction sites on the assay device upstream of the reaction site at which the reagent is immobilized and the chromatographic medium is contacted with chromatographic solvent to transport the sample and the labelled material to the reaction site at which the second reagent is immobilized.

Sandwich-type assays may be practiced according to the method wherein the colloidal particle labelled material is capable of participating in a specific binding reaction with the analyte substance. Competitive binding assay methods may also be practiced wherein the colloidal particle labelled material is capable of participating in a specific binding reaction with the immobilized reagent. Kits may be produced and the method may also be practiced wherein the chromatographic medium comprises a second reaction site impregnated with a second reagent which is immobilized against solvent transport and is capable of selective reaction with the colloidal particle labelled material to render it in an immobilized form in the second reaction site where it may be detected. In sandwich-type assays, the presence of colloidal particle labelled material at the second reaction site acts as a control and confirms the reactivity of the first reagent. In competitive binding assays, the presence of colloidal particle labelled material at the second reaction site indicates the degree of competition between the analyte substance and the immobilized reagent.

Other methods and devices are provided according to the invention wherein labelled specific binding materials including, but not limited to, colloidal particle labelled and enzyme labelled materials are incorporated on the chromatographic medium of an assay device in a dry form which may be rapidly resolubilized and chromatographically transported along the medium by selected chromatographic solvents. Such specific binding assay devices comprise a chromatographic medium having capillarity and the capacity for chromatographic solvent transport of one or more non-immobilized reagents and reactive sample components by means of a selected chromatographic solvent. The devices also comprise a first reaction site impregnated with a dried solution of a labelled material in the presence of a meta-soluble protein wherein the labelled material is capable of rapid solubilization and chromatographic solvent transport in the solvent and a second reaction site at which is immobilized a reagent capable of binding with a member selected from the group consisting of the analyte substance and the labelled material. The device may be used by (a) contacting the sample with the chromatographic medium; (b) solubilizing the labelled material and chromatographically transporting at least a portion of the labelled material to the second reaction site for binding thereto; and (c) determining the detectable response produced by said labelled material at the second reaction site as an indication of the presence or amount of the substance in the sample.

It is to be understood that the sample to be analyzed may be mixed with the chromatographic solvent and that the chromatographic medium may be contacted to the mixture of both. It is to be further understood that the chromatographic solvent may be replaced by said sample, said sample being capable of solubilizing said immobilized first reagent and chromatographically transporting itself and said labelled first reagent to the second zone at which the second reagent is disposed.

A preferred embodiment of the present invention is that wherein the chromatographic solvent is replaced by the sample which is capable of solubilizing the dried labelled material and transporting the analyte substance and the labelled material to the second reaction site containing the immobilized reagent.

Sandwich-type assays may be practiced according to the method wherein the labelled material is capable of participating in a specific binding reaction with the analyte substance. Competitive binding assay methods may also be practiced wherein the labelled material is capable of participating in a specific binding reaction with the immobilized reagent. Devices may be produced and methods may also be practiced wherein the chromatographic medium comprises a third reaction site impregnated with a second reagent which is immobilized against solvent transport and is capable of selective reaction with the labelled material to render the labelled material in an immobilized form at the third reaction site where it can be detected. In sandwich-type assays, the presence of labelled material at the third reaction site acts as a control and confirms the reactivity of the labelled material. In competitive binding assays, the presence of labelled material at the third reaction site indicates the degree of competition between the analyte substance and the labelled reagent.

The invention also provides a method for the stable storage of labile proteins including antibodies, antigens, and enzyme labelled and colloidal particle labelled specific binding materials wherein the protein materials may be rapidly solubilized by application of a suitable solvent. The method comprises drying the protein material, preferably under a stream of air, on a substrate in the presence of an aqueous medium containing a meta-soluble protein. The resulting product comprises a solid substrate upon which is impregnated and dried a labile protein in the presence of an aqueous medium containing a meta-soluble protein. The substrate may generally be any solid material such as glass or plastic but is preferably a porous or fibrous matrix such as paper or nitrocellulose. The solid substrate may be in various forms such as strips, pellets or the wall of a test tube or microtiter well. The aqueous solution containing the meta-soluble protein, preferably casein, may optionally comprise chromatographic transport facilitating agents such as polyethylene glycol, gelatin, bovine serum albumin and detergents.

Mix and Run Assay Devices (Sandwich-Type)

According to one aspect of the present invention, specific binding assays may be conducted according to mix and run techniques wherein an indicator solution comprising a colloidal particle labelled first specific binding reagent dissolved in a chromatographic transport facilitating agent is mixed with the analyte substance containing sample. Assay devices according to the invention are then dipped in the mixture of sample and indicator solution which is chromatographically transported to a first zone where a second reagent has been immobilized. According to one embodiment of a sandwich-type assay procedure, the first and second reagents are capable of specific binding with the analyte. In this embodiment, the labelled first reagent binds with the analyte after they have been mixed. The conjugate of the labelled first reagent and the analyte is then subjected to being immobilized by reaction with the second reagent and producing a visually detectable signal at the first zone. In the absence of analyte, labelled first reagent will not bind at the zone and no signal will be produced there. Alternative sandwich-type assay procedures may be followed wherein a third reagent which is specifically reactive with the labelled first reagent is immobilized at a second zone to provide a control. Still other, competitive-type assay methods and devices are provided where the immobilized second reagent is specifically reactive with both the analyte and the labelled first reagent which compete for binding with the immobilized reagent.

Referring to the drawing, FIGS. 1a, 1b and 1c depict a test device (10) for the detection of an analyte in a sample liquid comprising a length of chromatographic substrate material (11) with a first end (14) at which chromatographic solvent transport begins, a second end (15) at which chromatographic solvent transport ends and a first zone (13) impregnated with a second reagent which is immobilized against solvent transport and is capable of selective reaction with the analyte so as to render the analyte in an immobilized form. The device further comprises an inert support strip (12) to which the length of chromatographic material (11) is affixed.

According to a procedure for use of the device (10), a quantity of the sample to be tested is mixed with an indicator solution comprising a colloidal particle labelled first reagent and a chromatographic transport facilitating agent. The quantity and concentration of the chromatographic transport facilitating agent in the indicator solution added to the sample is selected such that it prevents aggregation and provides for rapid chromatographic solvent transport of the colloidal particle labelled specific binding reagent. In sandwich-type mix and run assays, the labelled first reagent will react-to specifically bind with the analyte. The test device (10) is then dipped at its first end (14) into a container (16) containing the mixture of sample and indicator solution (17) and the sample/indicator solution mixture containing the labelled first reagent/analyte conjugate progresses through the chromatographic material (11) to the first zone (13). The second specific binding reagent immobilized at the first zone (13) is also specifically reactive with the analyte and will react with the analyte or with first reagent/analyte conjugate to immobilize it at the first zone (13). The chromatographic solvent transport is such, however, that labelled first reagent which is not conjugated with the analyte along with other sample and indicator solution materials which are not immobilized at the first zone (13) are transported away from that zone. Chromatographic solvent transport continues until the sample/indicator solution mixture is depleted or until the sample/indicator solution front reaches the second end (15) of the device.

Analyte present in a sample will bind with the labelled first reagent and will be chromatographically transported to the first zone (13) where it will be immobilized by a specific binding reaction with the second reagent. Where sufficient analyte is present in a sample, the number of colloidal particles thus immobilized at the first zone (13) will be such as to produce a visually detectable signal. Of course, if no analyte is present in the sample, neither analyte nor labelled first reagent will be immobilized at the first zone, and no signal will be produced.

Mix and Run Assay Devices (Competition-Type)

The device (10) according to FIG. 1 may also be modified to perform competition-type specific binding assays. Specifically, the colloidal particle labelled first reagent may be selected to compete with the analyte for binding with the immobilized second reagent. Referring to the drawing, FIG. 1 depicts a test device for performing mix and run competition-type assays. The device itself and the identity of the immobilized second reagent is the same in the competition-type assay as in the sandwich-type assay. The only difference in the assay kits lies in the identity of the colloidal particle labelled first reagent material. In the sandwich-type assay kits of the invention, the labelled first reagent is specifically reactive with the analyte while in competition-type assays the labelled first reagent is a specific binding analogue of the analyte to be assayed and is specifically reactive with the immobilized second reagent in competition with the analyte.

According to a procedure for use of the device (10), a quantity of the sample to be tested is mixed with an indicator solution comprising a colloidal particle labelled first reagent in the presence of a chromatographic transport facilitating agent. The test device (10) is then dipped at its first end (14) into a container (16) filled with the mixture of sample and indicator solution (17). The sample/indicator solution mixture containing the labelled first reagent and the analyte progresses through the chromatographic substrate material (11) to the first zone (13). The labelled first reagent and the analyte then compete to bind with the second specific binding reagent immobilized at the first zone (13). The chromatographic solvent transport is such, however, that analyte and the colloidal particle labelled first reagent materials which do not bind specifically with the immobilized second reagent are removed from the first zone (13) by the chromatographic solvent. Chromatographic solvent transport will continue until the quantity of sample/indicator solution is depleted or until the solution front reaches the second end (15) of the device.

The quantity of analyte present in the sample will determine the amount of labelled first reagent which binds at the first zone (13). Adjustments of the quantity and/or binding affinity of the labelled first reagent can be made in order to determine the quantity of analyte present in the sample.

Alternative Mix and Run (Sandwich-Assay)

According to another aspect of the present invention, assay devices and kits are provided for performing sandwich-type assays which comprise a control function and which provide a positive or negative signal for the detection of a particular analyte. Referring to the drawing, FIG. 2 depicts a test device (20) comprising a length of chromatographic substrate material (21) with a first end (25) at which chromatographic solvent transport begins, and a second end (26) at which chromatographic solvent transport ends. The device also comprises a first zone (23) which may be separated and broken up into two or more areas and which is impregnated with a second reagent which is immobilized against solvent transport and is capable of selective reaction with the analyte so as to render the analyte in an immobilized form. The device (20) also comprises a second zone (24) which is impregnated with a third reagent which is immobilized against solvent transport and is capable of selective reaction with the colloidal particle labelled first reagent.

The first and second zones (23) and (24) may be shaped such as to provide a signal of distinctive shape when one but not the other or when both comprise an immobilized reagent. For example, the shapes of the first and second zones (23) and (24) are such in FIG. 2 that when label is immobilized at the second zone (24) only a minus (−) sign is indicated. When, on the other hand, label is immobilized at both the first (23) and second (24) zones a plus (+) sign is indicated.

It is preferred that the first zone impregnated with a reagent specifically reactive with the analyte to be detected be oriented essentially perpendicular to the direction of chromatographic flow. This is because the analyte and hence the labelled specific binding reagent tend to become immobilized at the leading rather than the trailing edge of the zone. Where an elongated zone is oriented with its major dimension parallel to the direction of chromatographic flow, the leading portion of the zone will trap a majority of the analyte with the result that the trailing end traps little analyte and the resulting visible signal has a shape which may be misinterpreted. By orienting the first zone perpendicular to the direction of chromatographic flow, a stronger and more distinct positive detection signal is produced.

According to a procedure for use of the device (20) a quantity of the sample to be tested is mixed with an indicator solution comprising a colloidal particle labelled first reagent in the presence of a chromatographic transport facilitating agent. The test device (20) is then dipped at its first end (25) into a container (27) containing a mixture of sample and indicator solution (28) and the sample/indicator solution containing the labelled first reagent/analyte complex progresses through the chromatographic material (21) to the first (23) and second (24) zones. The immobilized second reagent material at the first zone (23) is specifically reactive with the analyte and will immobilize the analyte as well as any analyte/labelled first reagent complex. In addition, the immobilized third reagent material at the second zone (24) is specifically reactive with the labelled first reagent and will immobilize the first reagent as well as any analyte/labelled first reagent conjugate.

Where analyte is present in the sample, analyte/labelled first reagent conjugate will form in the mixture of the indicator solution and sample and the conjugate will be immobilized at both the first (23) and second (24) zones thus, according to one embodiment, producing a plus (+) sign and positive signal. Where no analyte or less than a threshold amount is present in the sample, the first reagent will react with the third reagent at the second zone (24) and will be immobilized at that zone producing a visual signal. Because no analyte is present, nothing will be immobilized at the first zone (23) and no signal will be produced and only a minus (−) sign will appear indicating the absence of analyte. The presence of the signal at the second zone (24) but not the first (23) in addition to indicating absence of analyte will indicate the mobility of the labelled first reagent and will serve as a control relating to the utility of the assay device.

Alternative Mix and Run (Competitor-Type Assay)

According to another aspect of the present invention, assay devices and kits are provided for performing competition-type mix and run assays which comprise a first zone impregnated with a second reagent specifically reactive with the analyte to be detected and the colloidal particle labelled first reagent and one or more second zones impregnated with a third reagent specifically reactive with the labelled first reagent and not with the analyte.

Figure 3B:
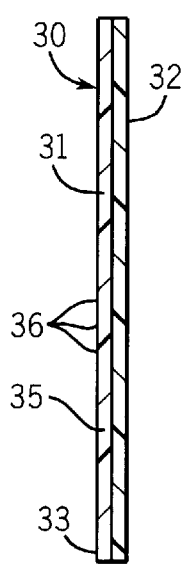
Figure 3C:
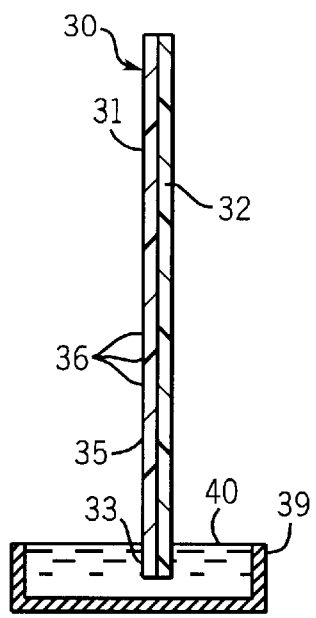

Referring to the drawing, FIGS. 3a, 3b and 3c depict a test device (30) for the detection of an analyte in a sample liquid (40). The device (30) comprises a length of chromatographic substrate material (31) with a first end (33) at which chromatographic solvent transport begins and a second end (34), (which is not necessarily the second physical end of the strip) at which chromatographic solvent transport ends. The device (30) further comprises a first zone (35) impregnated with a second reagent which is immobilized against solvent transport and is capable of selective reaction with a member of the group consisting of the analyte and a colloidal particle labelled first reagent. Downstream of the first zone (35) is located the second zone (36) which may optionally comprise more than one area and which is impregnated with a third reagent which is immobilized against solvent transport and is specifically reactive with the labelled first reagent but not with the analyte. The device also comprises a right-hand solvent barrier means (37) and a left-hand solvent barrier means (38) which focus the chromatographic flow of material from the first end (33) to the first (35) and second (36) zones. The solvent barrier means (37) and (38) also effectively lengthen the chromatographic substrate material (31) by providing extended chromatographic transport pathways to the second end (34).

According to a procedure for use of the device (30), a quantity of the sample to be tested is mixed with an indicator solution comprising a colloidal particle labelled first reagent in the presence of a chromatographic transport facilitating agent. The first reagent is a specific binding analogue of the analyte to be assayed and is specifically reactive with the immobilized second reagent at the first zone (35). The test device (30) is then dipped at its first end (33) into a container (39) filled with the mixture (40) of sample and indicator solution. The sample/indicator solution mixture containing the labelled first reagent and the analyte progresses through the chromatographic material (31) to the first zone (35). The colloidal particle labelled first reagent and the analyte then compete to bind with the second specific binding reagent immobilized at the first zone (35). The chromatographic solvent transport is such, however, that analyte and labelled first reagent materials which do not bind specifically with the immobilized second reagent are removed from the first zone (35) by the chromatographic solvent and are transported toward the second end (34) and to the second zone(s) (36). The labelled first reagent, which can be a mouse anti-second reagent antibody when the analyte to be detected is a human anti-second reagent antibody, then reacts with the third reagent (which can be anti-mouse IgG antibodies) immobilized at the second zone (36) which is specifically reactive with the labelled first reagent but not the analyte. The third reagent reacts with the labelled first reagent immobilizing it at the second zone (36) producing a detectable signal. The device may optionally comprise additional "second zones" such that where an excess of labelled first reagent is mixed with the sample material and the labelled first reagent is partially or wholly displaced from binding at the first zone (35), the degree of displacement may be determined from the extent of binding at the second zone(s) (36). Chromatographic solvent transport will continue and the sample/indicator solution will progress through the device until the quantity of sample/indicator solution is depleted or until the solution front progresses around the right-hand (37) and left-hand (38) solvent barrier means and reaches the second end (34) of the device.

Pre-Impregnated Labelled Specific Binding Material Devices

An alternative aspect of the present invention relates to specific binding assay devices wherein labelled specific binding reagents including those with colloidal particle or enzyme labels which are capable of chromatographic solvent transport are impregnated and dried onto the chromatographic substrate materials of the devices. It has surprisingly been found that drying of the labelled specific binding reagent materials in the presence of meta-soluble proteins, such as casein, not only provides for the rapid chromatographic solvent transport of labelled materials, but also provides for the rapid resolubilization of such labelled materials impregnated and dried onto the chromatographic substrate materials. The labelled reagents thus resolubilized are capable of being efficiently transported by means of conventional chromatographic solvent systems and of reacting in the specific binding assays.

The ability to impregnate chromatographic substrate materials with the labelled specific binding reagents, which may then be resolubilized, makes possible the practice of a variety of assay procedures which avoid the use of labelled reagent addition steps. Both sandwich-type and competition-type assays may be conducted using the kits and strips of the present invention.

Sandwich Assay Device

Figure 4A:
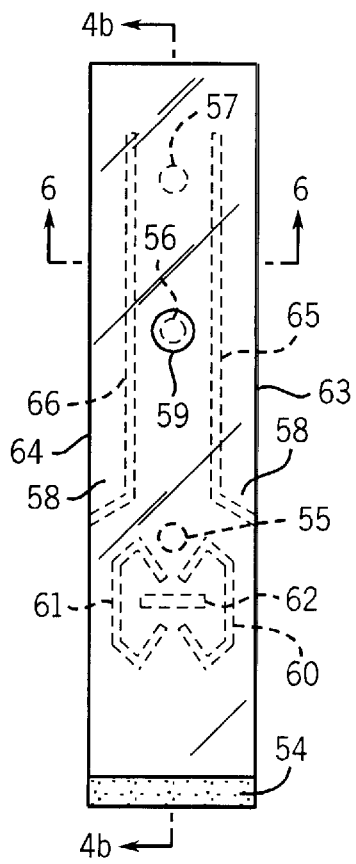
Figure 4B:
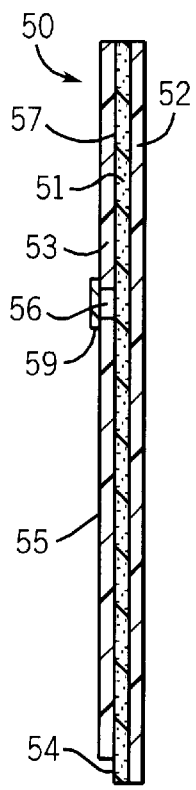
Figure 4C:
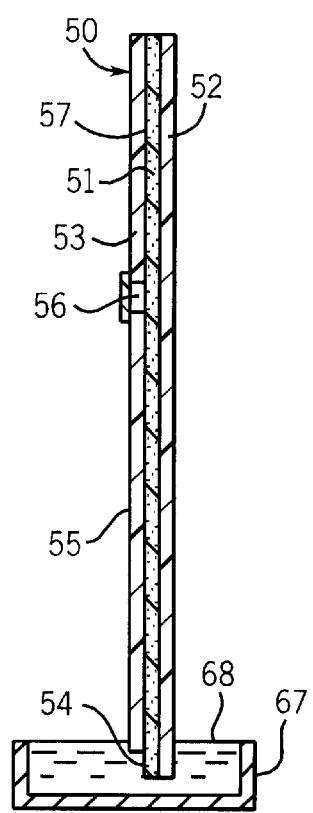
FIGS. 4c and 5c are cross-sectional views of the test devices shown in FIGS. 4a and 5a, respectively, in contact with a volume of chromatographic solvent.

Referring to the drawing, FIGS. 4a, 4b and 4c depict a test device (50) for the detection of an analyte in a sample wherein a labelled first reagent is impregnated and dried onto the device (50). The device (50) comprises a length of chromatographic substrate material (51) with a first end (54) at which chromatographic solvent transport begins and second ends (58) at which chromatographic solvent transport ends. The length of material (51) comprises a first zone (55), a second zone (56) and a third zone (57).

Between the first end (54) and the first zone (55) is a delaying box defined by a right-forward solvent barrier means (60), a left-forward solvent barrier means (61) and a transverse solvent barrier means (62). The right-forward solvent barrier means (60) and the right edge (63) of the material define a right-hand chromatographic solvent transport pathway, and the left-forward solvent barrier means (61) and the left edge (64) of the material define a left-hand chromatographic solvent transport pathway. The right-hand and left-hand chromatographic solvent transport pathways meet downstream of the first zone (55) and the delaying box to form a center chromatographic transport pathway in which are located said second (56) and third (57) zones defined by a right-rearward solvent barrier means (65) and a left-rearward solvent barrier means (66). Downstream of the third zone (57), the right-rearward solvent barrier means (65) and the right edge (63) and the left-rearward solvent barrier means (66) and the left edge (64) define chromatographic solvent transport pathways leading to second ends (58) at which chromatographic solvent transport ends.

The first zone (55) is impregnated with a labelled first specific binding reagent which is mobile in a chromatographic solvent (68) and is capable of reaction with and immobilization against solvent transport by the analyte when the analyte is in immobilized form. The second zone (56) is downstream of the first zone (55) and provides a suitable site for receiving the sample to be analyzed. The third zone (57) is downstream of the second zone (56) and is impregnated with a second reagent which is immobilized against solvent transport and is capable of selective reaction with the analyte so as to render the analyte in an immobilized form. The device further comprises an inert support strip (52) to which the length of chromatographic substrate material (51) is affixed. The device additionally comprises a cover plate (53) which may optionally be transparent and may be placed over the length of the chromatographic material (51) leaving exposed the first end (54) of the material. The cover plate (53) defines an opening corresponding to and leaving exposed the second zone (56). A removable tab (59) covers the second zone (56).

According to a procedure for use of device (50) of FIGS. 4a, 4b and 4c, the first tab (59) is removed from the device (50), a sample of the material to be tested is applied to the second zone (56) and the removable tab (59) is replaced. The device (50) is then contacted at its first end (54) into a container (67) of chromatographic solvent (68). The chromatographic solvent (48) then progresses through the length of chromatographic material passing along the right-hand and left-hand chromatographic solvent transport pathways to the center chromatographic transport pathway. Some of the solvent is transported upward toward the second zone (56) while some of the solvent is transported downward toward the first zone (55) solubilizing the labelled first reagent. A portion of the chromatographic solvent (68) from the first end (54) passes between the right-forward solvent barrier means (60) and left-forward solvent barrier means (61) into the delaying box. The chromatographic solvent passes around the transverse solvent barrier means (62) which delays its flow before it is transported toward the first zone (55). The labelled first reagent at the first zone has already been solubilized by solvent from the right and left-hand solvent transport pathways and the solvent progressing through the delaying box upon reaching the solubilized first reagent starts to transport the first reagent toward the second zone (56). The chromatographic solvent (68) which was transported through the right-hand and left-hand solvent transport pathways then contacts the sample applied to the second zone (56) and transports the sample to the third zone (57). There, the immobilized second reagent material selectively reacts with analyte present in the sample so as to immobilize it. Non-analyte components of the sample are transported away from the third zone (57). The labelled first reagent is then transported to the third zone (57) where it is immobilized against solvent transport by the analyte when any analyte is in immobilized form. Chromatographic solvent transport of the analyte-depleted sample and first reagent continues until the chromatographic solvent (68) reaches the second end (58) of the material.

A variety of sandwich-type assay devices including dried labelled reagents and preferably including dried enzyme labelled and colloidal particle labelled reagents may be produced according to the invention. It is frequently desirable to avoid premature contact of analyte and sample materials with the reagents and contact of the reagents with each other. Thus, the relative mobility of the sample components and the various reagents or the site relationship between the zones may be selected such that the reagents and sample components mix at only the times and locations desired. Co-owned U.S. Pat. No. 4,960,691 discloses various methods and devices for conducting chromatographic solvent transport assays where it is desired to avoid contact of a labelled first reagent material (such as an anti-human immunoglobulin antibody) with sample material (such as serum) prior to the time at which the analyte antibody is immobilized against solvent transport at a reaction zone and other non-analyte antibodies contained in the serum sample are cleared from the third zone by chromatographic solvent transport. The use of acceleration and delay pathways can also be particularly useful in preventing drying of sample materials or other reagents.

Competition Assay Device

The assay devices of the present invention comprising solubilizable specific binding reagents are also suitable for the practice of competitive binding type assays. According to such methods, the immobilized second reagent is selected, as in sandwich-type assays, so as to specifically bind with the analyte of interest. The labelled first reagent, however, is selected to be a specific binding analogue of the analyte which will bind competitively with the immobilized second reagent. In carrying out competition type assays according to the invention, it is generally not necessary that the analyte and the colloidal particle labelled reagent be prevented from contacting each other prior to their contacting the immobilized second reagent. Thus, the device may be designed so as to mix the analyte containing sample and the labelled first reagent. Of course, if so desired, the device may be designed so as to prevent contact of the sample and labelled first reagents until after their contacting the immobilized second reagent.

Figure 5A:
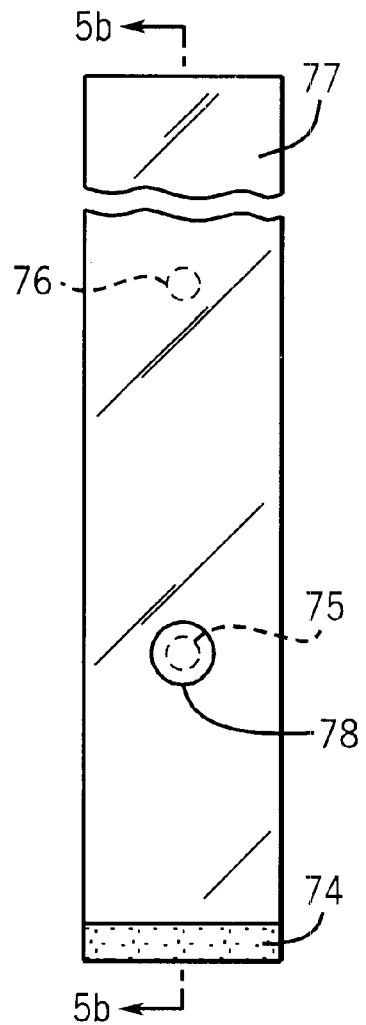
Figure 5B:
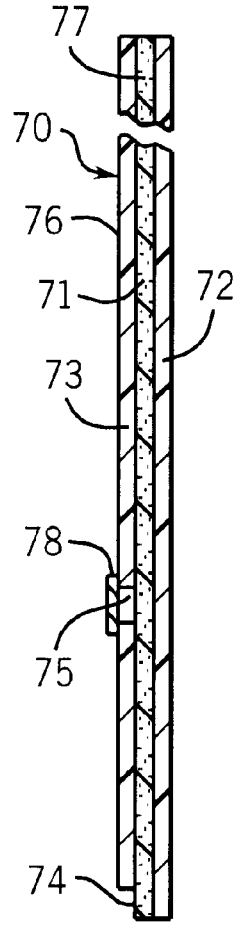
Figure 5C:
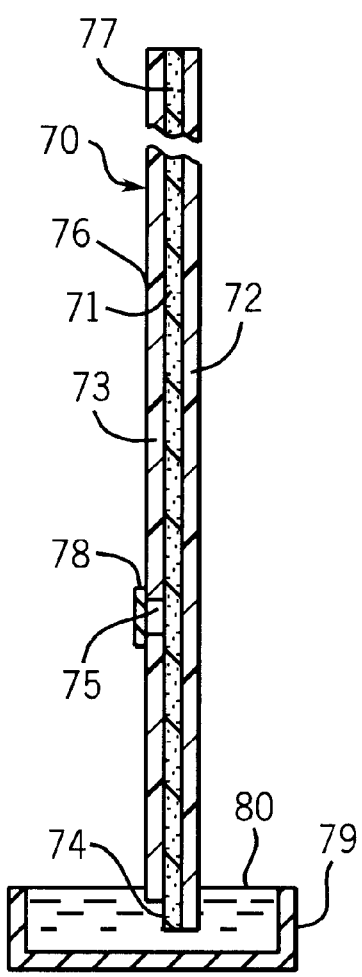
Figure 6:
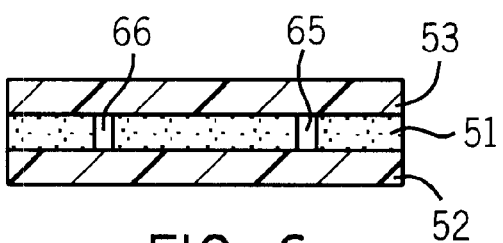
FIG. 6 is a cross-sectional view of the test device of FIG. 4a taken along lines 6—6.

Referring to the drawing, FIGS. 5a, 5b and 5c depict a test device (70) for conducting competitive binding assays for detection of an analyte in a sample wherein a labelled first reagent is impregnated and dried onto the device (70). The device (70) comprises a length of chromatographic substrate material (71) with a first end (74) at which chromatographic solvent transport begins and a second end (77) at which chromatographic solvent transport ends. The length of material (71) comprises a first zone (75) and a second zone (76). The first zone is impregnated with a labelled first reagent in the presence of a meta-soluble protein containing anti-aggregation buffer. The second zone (76) is downstream of the first zone (75) and is impregnated with a second reagent which is capable of a selective binding reaction with both the analyte and the labelled first reagent so as to render the analyte and labelled first reagent in immobilized form. The device further comprises an inert support strip (72) to which the length of chromatographic substrate material (71) is affixed. The device additionally comprises a cover plate (73) which is placed over the length of the chromatographic substrate material (71) leaving exposed the first end (74) of the material. The cover plate (73) defines an opening corresponding to and leaving exposed the first zone (75) which is covered by a removable tab (78).

According to a procedure for use of device (70) of FIGS. 5a, 5b and 5c, the tab (78) is removed from the device (70), a sample of the material to be tested is applied to the first zone (75) and the tab (78) is replaced. The device (70) is then contacted at its first end (74) into a container (79) of chromatographic solvent (80). The chromatographic solvent (80) then progresses through the length of the chromatographic substrate material (71) transporting the labelled first reagent impregnated at the first zone (75) and the sample deposited there to the second zone (76). There the analyte and labelled first reagent compete to bind with the immobilized second reagent for which they are both specifically reactive. Non-analyte components as well as unbound analyte and first reagent material are transported away from the second zone (76) by means of the chromatographic solvent transport which continues until the chromatographic solvent is exhausted or the solvent front reaches the second end (77) of the material. At the conclusion of the chromatographic solvent transport, the second zone (76) may be observed to determine the presence of labelled first reagent immobilized at that location. The presence of labelled first reagent at that location may then be related to the presence of analyte in the sample. Where the first reagent is labelled with colloidal particles, its presence at the second zone may be observed directly. Where the first reagent is labelled with an enzyme label, other reagents such as enzyme substrates and indicator dyes may be added to the second zone to visualize the presence of the first reagent.

Description of the Colloidal Particles

The present invention is directed to means for improving the chromatographic transport characteristics of colloidal particles used as labels in specific binding assays. The colloidal particles that may be used in conjunction with the methods, kits and devices of the present invention are those which may be used with specific binding assays generally. Particularly well known is the use of colloidal metal particles and especially colloidal gold for carrying out immunoassays. Other colloidal particles such as polymerized dye particles which may also be used as labels in specific assay methods such as those of Hirschfeld, U.S. Pat. Nos. 4,166, 105 and Henry, 4,452,886, the disclosures of which are hereby incorporated by reference, may now be used in chromatographic transport specific binding assays. Particularly preferred colloidal particle labels for use with the present invention include non-metal particles such as selenium, tellurium and sulfur with selenium being particularly preferred according to co-owned U.S. Pat. No. 4,954,452, the disclosure of which is hereby incorporated by reference.

Colloidal particles which are suitable as labels according to the invention include those which may be conjugated to specific binding reagents without interfering with the activity of such reagents or with other reagents or analytes. The particles must be detectable and preferably produce a visually detectable signal when present in relatively low concentrations. Particles ranging in size from about 1 nm to about 200 nm in diameter are generally suitable although both larger and smaller particles are also suitable for use according to the invention. The methods of the invention are particularly useful with particles larger than about 1 nm in diameter which are particularly susceptible to aggregation. Particles larger than about 200 nm tend to exhibit diminished mobility and may tend to drop out of suspension even in the presence of the chromatographic transport facilitating agents of the present invention. Particles much larger may also have their transport limited by the pore size of the chromatographic transport material. Particles smaller than about 1 nm tend to exhibit superior chromatographic mobility to larger particles and in some cases may not require the use of the chromatographic transport facilitating agents of the present invention. Nevertheless, particles smaller than about 1 nm tend to provide weaker signals and are thus less suitable for use in assay procedures.

Colloidal metal particles are particularly suitable as labels according to the present invention and include those particles which are comprised of metals or metal compounds including metal oxides, metal hydroxides or metal salts. Such particles generally vary in diameter from about 1 nm to about 200 nm with particles ranging in diameter from about 40 nm to about 80 nm being particularly preferred. Particles may comprise pure metal or metal compounds but may also comprise polymer nuclei coated with metal or metal compounds. Such particles are disclosed to have properties similar to those of particles comprising pure metal or metal compounds. Suitable metals and metal compounds include those selected from the group consisting of the metals platinum, gold, silver and copper and the metal compounds, silver iodide, silver bromide, copper hydroxide, iron oxide, iron hydroxide or hydrous oxide, aluminum hydroxide, or hydrous oxide, chromium hydroxide or hydrous hydroxide, lead sulfide, mercury sulphide, barium sulphate and titanium dioxide. Preferred metal particles include those made up of gold silver or iron oxide.

Colloidal metal particles may be produced according to methods generally known in the art. Specifically, Frens, Nature, 241, 20 (1973) the disclosure of which is hereby incorporated by reference discloses methods for the production of gold sol particles of varying sizes. Gold particles may be produced by methods wherein a solution of gold chloride is heated to boiling and is then mixed with a solution of sodium citrate to reduce the gold chloride. Soon after mixing of the two solutions the boiling solution turns a faint blue indicating the onset of nucleation soon thereafter the blue color changes to red indicating the formation of monodisperse particles. Reduction of the gold chloride is complete after only a few more minutes of boiling. The resulting particle sizes may be controlled by variation of the concentration of the sodium citrate solution. Particles comprising other metals and metal compounds as well as particles comprising polymer nuclei may be obtained by similar methodologies. The colors of the visually detectable signal from the metal particle label is dependent upon the identity and particle size of the metal particle. For example, colloidal gold particles produce colors varying from orange to red to violet depending upon the particle size of the sol.

Non-metal colloidal particles such as those of selenium, tellurium and sulfur may be produced according to the methods of co-owned U.S. Pat. No. 4,954,452.

Conjugation of Binding Reagents with the Colloidal Particles

The specific binding reagents of the invention may be conjugated with colloidal particle labels according to methods generally known in the art. According to one general procedure, proteinaceous specific binding reagents and colloidal particles are rapidly mixed together and are incubated in a solution to which an agent such as bovine serum albumin or polyethylene glycol is added. The suspension is centrifuged first at low speed so as to remove any large aggregates and then at high speed to produce a pellet of the reagent/colloidal particle conjugate before the supernatant is aspirated and removed. The pellet is resuspended in a solution containing a chromatographic transport facilitating agent according to the invention.

The colloidal particle labels need not be conjugated directly to the specific binding reagents but may be coated or pretreated with other reagents. Leuvering, U.S. Pat. No. 4,313,734, the disclosure of which is hereby incorporated by reference, discloses methods by which metal sol particles may be coated with inert polymer and copolymer coatings. The metal sol may be brought into contact with the polymer or the sol can be placed in an environment containing one or more monomers and a polymerization reaction initiated. After coating with the inert polymer the immunological specific binding component may be coupled to the coating material by adsorption or covalent binding.

Description of the Meta-Soluble Proteins

As used herein, the term meta-soluble protein refers to those proteins which, in their native form, are hydrophobic and poorly soluble in water but which when subjected to chemical treatment, as by alkaline purification treatment, can be made more hydrophilic and thus capable of forming uniform solutions or dispersions in water. Such chemical treatments serve to cleave hydrophobic fatty acid groups from the protein molecules by cleavage of ester or other linkages. This cleavage leaves carboxy and hydroxy residues on the molecule, rendering the protein more hydrophilic at those sites. Without intending to be limited to a single theory of the invention, it is believed that alkaline treatment renders the meta-soluble proteins somewhat detergent-like, that is, presenting both hydrophobic and hydrophilic aspects. Chemical treatment, while required for practice of the invention, need not be alkaline treatment but may also be with acids, detergents or solvents such as alcohol or urea.

The proteins, when so treated, are capable of functioning as potent chromatographic transport facilitating agents thus preventing aggregation and inactivation of labile proteins and reagents such as enzyme and colloidal particle labelled reagents. In addition, the treated meta-soluble proteins when dried with a labile protein material, provides for the stable storage and prevents aggregation and inactivation when maintained in a dry state while allowing the protein materials to be rapidly resolubilized and utilized in chromatographic transport assays if so desired. The labile protein materials include antibodies, antigens or other specific binding proteins including such proteins labelled with enzymes, colloidal particles or other labels. Preferred meta-soluble proteins include materials such as casein, zein and a non-albumin component of egg white protein with casein in concentrations of from 1 to 5% being particularly preferred for use with the invention. Preferred materials include vitamin free casein (Sigma Chemical Co., St. Louis, Mo., catalogue No. C-3400), Zein (Sigma, catalogue No. Z-3625) and egg white protein (Sigma, catalogue No. A-5253) which comprises both the meta-soluble protein responsible for solubilization and transport and the inactive albumin fractions. It is known that the egg white component responsible for solubilization and transport is not egg white albumin as the pure albumin material does not promote resolubilization and transport.

Description of the Chromatographic Transport Facilitating Agents

As used herein, the term chromatographic transport facilitating agents refers to those materials which prevent aggregation and inactivation of specific binding materials and reagents in solution and, further, which promote their chromatographic transport. The agents may be liquids or may be solids, in which case they are preferably dissolved in a solution such as a buffer salt solution. Suitable chromatographic transport facilitating agents include materials such as polyethylene glycol, proteinaceous materials such as gelatin and bovine serum albumin and detergents such as sodium dodecyl sulfate (SDS), sodium deoxycholate (DOC) and polyethylene glycol tert-octylphenyl ether (TRITON X-100). Particularly preferred is the use of meta-soluble protein materials such as casein. Meta-soluble proteins may also be used to impregnate and dry labelled reagents onto solid substrate materials including chromatographic substrate materials in such a manner that the labelled reagents may be rapidly resolubilized and transported, if desired, by means of chromatographic solvent transport.

Where the chromatographic transport facilitating agent is to be mixed with the labelled material and utilized as a component of an indicator solution with mix and run kits, it preferably comprises casein or another treated meta-soluble protein in combination with other chromatographic transport facilitating agents such as PEG with buffer salt solution. A particularly preferred chromatographic transport facilitating buffer comprises 2% casein in combination with 0.1% PEG in PBS. The concentration of the components of the buffer and of the indicator solution are selected in the practice of the mix and run kits of the invention such that for a given sample size sufficient concentrations of the components are provided to prevent aggregation and inactivation of the labelled reagents and promote their chromatographic solvent transport.

Colloidal particle labelled specific binding reagents in the presence of casein containing solutions can have Rf values approaching 1.0 while colloidal labelled materials in buffers containing PEG can have Rf values approaching 0.7. Casein concentrations in suitable chromatographic transport facilitating buffers range from between about 0.1% (w/v) to greater than about 5% with concentrations of about 2% being preferred. It is noted that concentrations greater than about 5% do not appear to assist the anti-aggregation or chromatographic transport facilitating qualities of the buffer while they may, however, tend to interfere with resolubilization of labelled reagents dried onto the test strips of the invention.

Solutions comprising PEG as the only chromatographic transport facilitating agent are suitable for practice of some aspects of the present invention. PEG containing buffers have Rfs as high as 0.7. Preferred PEG concentrations in suitable chromatographic transport facilitating buffers range from about 0.05% to about 2% with about 1% being preferred. Suitable PEG polymers may have a variety of molecular weights, with molecular weights of about 20,000 being particularly preferred.

Gelatin is generally unsuitable for use alone as a chromatographic transport facilitating agent as solutions containing it provide for an Rf of only about 0.2. It may nevertheless be useful when combined with other anti-aggregation materials of the invention. Gelatin is generally unsuitable, however, when used in concentrations greater than about 2% as it contributes to the tendency to aggregate.

Buffer solutions suitable for use with the chromatographic transport facilitating agents of the invention should have a pH between about 5 and 9 and should not interfere with the reactivity of the analyte or reagents or their chromatographic transport. Preferred buffer solutions have pHs of about 7 and include buffers such as Tris and PBS.

Description of the Chromatographic Media

Chromatographic media useful with the present invention include those chromatographic substrate materials having capillarity and the capacity for chromatographic solvent transport of non-immobilized reagents and reactive sample components by means of a selected chromatographic solvent. The chromatographic substrate materials used with the invention are preferably in the form of strips, but it is contemplated that they may be in other forms including, but not limited to, particles or gel materials in a chromatographic column. While a wide variety of chromatographic strip materials such as woven and non-woven fibrous materials used for paper chromatography are suitable for use with the invention, the use of microporous or microgranular thin layer chromatography substrates is particularly preferred as the use of such substrates improves the speed and resolution of the assays according to the invention. The materials should preferably be inert and generally not react physically or chemically with any of the sample components, reagents, colloidal particle labels, buffers or reaction products.

Thin layer chromatographic substrate materials particularly suitable for use with the present invention include granular thin layer chromatographic materials such as silica or microgranular cellulose. Preferred non-granular microporous materials include microporous cellulose esters, for example, esters of cellulose with an aliphatic carboxylic acid, such as an alkane carboxylic acid, having from 1 to 7 carbon atoms, e.g., acetic acid, propionic acid, or any of the butyric acids or valeric acids. Especially preferred are microporous materials made from nitrocellulose, by which term any nitric acid ester of cellulose is intended. Suitable materials include nitrocellulose in combination with any of the said carboxylic acid cellulose esters. Thus, pure nitrocellulose esters can be used as consisting of an ester of cellulose having approximately 3 nitric groups per 6 carbon atoms. Most preferred is a Type SMWP material (Millipore Corp., Bedford, Mass.) which has a pore size of 5 $\mu$m.

The various chromatographic substrate materials may be used as such in suitable shapes such as films, strips or sheets. They may also be coated onto or bonded or laminated to appropriate inert support materials such as paper, glass, plastic, metal or fabrics. (One preferred inert support material is Mylar.) Such a support material not only has the effect of providing structural support to the chromatographic substrate material but also prevents evaporation of reagent and solvent materials during the assay procedure. Cover plates may also be fashioned of such inert materials. Cover plates, although not required for practice of the invention, lend additional structural support and further prevent evaporation of reagent and solvent materials during the assay procedure. Such cover plates may be transparent for viewing the progression of the assay and may comprise ports for addition of sample materials, chromatographic solvent or reagents.

The chromatographic medium upon which the assays are conducted may be any shape or size but is preferably in the form of strips of thickness in the range of from about 0.01 mm to about 0.5 mm, and most preferably of about 0.1 mm. The strips may vary widely in their other dimensions but are preferably kept fairly small in order to shorten the assay development time and minimize material usage. When the strips are extremely small in size they may be attached to a suitable handle or holder in order to aid in handling and observation of results. Strips approximately 3 mm wide and up to 75 mm long have been found to be particularly suitable in the fabrication of single pathway devices according to the present invention. The pore size may vary within wide limits but is preferably between about 0.05 $\mu$m and 20 $\mu$m and preferably about 5 $\mu$m. Pore size is limited on the lower end by the size of the transported analytes, reagents and colloidal particle labels. If the pore size is too small, assay materials will be transported slowly or not at all. On the higher end, pore size is limited by binding capacity. It is generally desired that chromatographic transport be rapid with the transport and assay being completed within less than five minutes, and preferably less than or about two minutes. Chromatographic transport should not be so rapid that specific binding capacity is lost as reagents do not have time to specifically bind with one another. The combination of pore size and substrate thickness may thus be varied according to the characteristics of the chromatographic solvents, specific reagents, sample materials and colloidal particle labels used in order to obtain desired properties of speed and resolution.

It is desired that in forming the strip materials of the present invention that any irregularities in the materials or in the edges of the materials which might cause uneven flow through the material be avoided. Means of fashioning the strip materials include the use of a paper cutter with a tungsten carbide rotary blade. A preferred means, however, involves the use of laser cutting which is particularly suitable for use in mass production techniques.

Because the chromatographic media of the device is preferably chemically inert, it may have to be activated at any zone where it is desired to immobilize a specific binding reagent against solvent transport. Various methods will be required to render the reagent immobilized according to the particular chemical nature of the substrate material and the second reagent. Generally, when the media is nitrocellulose or a mixed nitrocellulose ester, no special chemical linkage is required for the immobilization of reagents. Various techniques may be used for other materials and reagents which include functionalization with materials such as carbonyldiimidazole, glutaraldehyde or succinic acid, or treatment with materials such as cyanogen bromide. Other suitable reactions include treatment with Schiff bases and borohydride for reduction of aldehydic, carbonyl and amino groups. DNA, RNA and certain antigens may be immobilized against solvent transport by baking onto the chromatographic material. Baking may be carried out at temperatures ranging from about 60° C. to about 120° C. for times varying from about five minutes to about 12 hours, but preferably at about 80° C. for about two hours.

Solvent Transport Barriers

Various means are known for achieving the sequential transport of reagents and sample materials such as are disclosed in co-owned U.S. Pat. No. 4,960,691.

Solvent barriers which block chromatographic flow according to the invention may be formed by various physical or chemical etching techniques. Gaps of less than 0.1 mm in width have been found to prevent the flow of liquid. A preferred means for forming such barriers involves the use of laser etching techniques. A $CO_2$ laser may be used according to one procedure wherein Mylar backed nitrocellulose is mounted on a supporting fixture which is mounted on a computer controlled X-Y table capable of very close positioning tolerances. Alternatively, a beam moving mechanism may be used. Using a combination of suitable optical lenses and careful beam focusing, a laser beam spot, with a diameter of approximately 0.005 inches, can be focused on the nitrocellulose. By careful control of the laser power, a narrow path of nitrocellulose, approximately 0.005 inches wide, can either be removed from or melted to the Mylar backing. The use of a $CO_2$ laser is particularly preferred because of the favorable coupling effect of light from the laser with the nitrocellulose. Nevertheless, other types of lasers are suitable, provided that the laser beam wavelength produces the desired effect on the solvent transport material. Through use of a moving beam or an X-Y table, precision paths baffled channels or other intricate shapes may be generated on the nitrocellulose.

Description of the Specific Binding Reagents

Specific binding reagents useful with the present invention include those materials which are members of a specific binding pair consisting of a ligand and a receptor. The ligand and receptor are related in that the receptor specifically binds to the ligand, being capable of distinguishing the ligand from other materials having similar characteristics. The methods, kits and devices according to the present invention are particularly useful in the practice of immunological assay techniques where the specific binding reagents are antigens and antibodies. Specific binding materials such as avidin, biotin, streptavidin and antibiotin may also be labelled with colloidal particles and utilized in chromatographic solvent transport assays according to the invention. The methods, kits and devices may also prove useful in the practice of DNA and RNA hybridization assays and other specific binding assays such as those involving receptors for hormones or other biologically active agents.

Antibodies useful in conducting the immunoassays of the present invention include those specifically reactive with various analytes the detection of which in biological fluids is desired. Such antibodies are preferably IgG or IgM antibodies or mixtures thereof, which are essentially free of association with antibodies capable of binding with non-analyte molecules. The antibodies may be polyclonal or monoclonal and are commercially available or may be obtained by mouse ascites, tissue culture or other techniques known to the art. A typical description of hybridoma procedure for the production of monoclonal antibodies may be found in Wands, J. R., and V. R. Zurawski, Gastroenterology 80:225 (1981); Marshak-Rothstein, A., et al.; J. Immunol. 122:2491 (1979); Oi, V. Y. and L. A. Herzenberg, "Immunoglobulin Producing Hybrid", Mishell, B. B. and S. M. Shiigi (eds.) *Selected Methods in Cellular Immunology*, San Francisco: W. H. Freeman Publishing, 1979; and U.S. Pat. No. 4,515,893 issued to Kung, et al. The use of mixtures of monoclonal antibodies of differing antigenic specificities or of monoclonal antibodies and polyclonal antibodies may be desired. It is further contemplated that fragments of antibody molecules may be used as specific binding reagents according to the invention including half antibody molecules and Fab, Fab' or F(ab')$_2$ fragments known in the art. Regardless of the particular source or type of antibodies, however, it is preferred that they be generally free of impurities. The antibodies may be purified by column chromatographic or other conventional means but are preferably purified according to known affinity purification techniques.

Antigens and haptens useful in carrying out the immunoassays of the present invention include those materials, whether natural or synthesized, which present antigenic determinants for which the analyte antibodies are specifically reactive when presented on the chromatographic strip materials of the invention. Synthesized antigens include those which are constructed according to conventional chemical syntheses as well as those constructed according to recombinant DNA techniques. Antigen materials may also be labelled with enzymes and colloidal particles according to the invention and used in sandwich type assays for the detection of antibody analytes or in competition assays for the detection of antigen analytes.

The methods and devices according to the present invention are expected to be useful in the practice of a wide variety of specific binding assays including nucleic acid hybridization assays. DNA and RNA hybridization materials useful according to the present invention would include DNA and RNA polynucleotide probes having base sequences generally complementary to those of analyte gene materials. The probes of the invention will generally have between about 25 and about 10,000 bases and preferably between about 30 and about 5,000 bases. The probes need not be perfectly complementary to the base sequences of analyte gene materials and will generally hybridize provided about 70% or greater homology exists between the base sequences. Conditions relating to DNA and RNA hybridization are disclosed generally in Crosa, et al., J. Bact. 115(3), 904–911 (1973). Polynucleotide probe materials may be obtained according to techniques well known in the art. See, e.g., Kornberg, DNA Replication, W. H. Freeman and Co., San Francisco, 670–679 (1978); Dallas, et al., J. Bacteriol. 139, 850–858 (1979) and So, et al., Nature, 277, 453–456 (1979).

Description of Blocking Agents

Blocking agents useful in preparation of devices for the specific binding of the present invention are those agents capable of blocking excess binding sites on the chromatographic media which might hinder chromatographic solvent transport of sample materials or reagents of the invention. It is generally not necessary to block the chromatographic substrate material in the practice of mix and run assays where the specific binding reagents are mixed with the sample material and the chromatographic solvent. Blocking of excess binding sites on the chromatographic solvent material is particularly useful, however, where the sample or any reagents are impregnated on the strip in the absence of chromatographic solvent. In the construction of devices of the present invention, the chromatographic media is impregnated with the reagent(s) to be immobilized at the location(s) desired. Once the reagent(s) has (have) been immobilized at the desired zones, the strip is then processed so as to block excess binding sites of the chromatographic material which might interfere with chromatographic solvent transport of other reagents or sample materials. Particularly suitable is the use of blocking solutions comprising proteins from sources such as casein, gelatin or total serum. Such proteins are selected to not interfere with or cross-react with reagent materials of the assays. Blocking of the sites may preferably be conducted by dipping the chromatographic substrate materials in a solution of 0.2% casein in physiological saline and air drying the strip materials. Other methods include dipping in solutions of 0.1% gelatin or 0.1% BSA followed by air drying of the substrate materials.

Description of the Chromatographic Solvent System

Kits for performing "dip and run" assays according to the invention utilize mixtures of the sample materials and indicator solutions themselves for chromatographic transport of the mobile elements of the assays. Where the assay devices are not of the dip and run format and sample materials are applied in smaller quantities to locations not at the first end of the assay devices, chromatographic solvents are required for transport of the various reagents and sample components on the assay devices.

Suitable chromatographic solvent systems for specific binding assays according to the invention are those capable of solubilizing the analyte, labelled reagents and any additional reagents and materials and transporting them on the chromatographic material. Such solvents should have sufficient ionic strength to prevent electrostatic interaction of the transported materials with the strip material. A preferred solvent for use in immunoassay procedures according to the invention is physiological saline solution with a pH in the neutral range. Proteins as well as detergents such as sodium dodecyl sulfate (SDS), polyethylene glycol tert-octyiphenyl ether (TRITON X-100) and sodium deoxycholate (DOC) may be incorporated in the chromatographic solvent in quantities which minimize non-specific binding with the strip material but not in such excess as would prevent the desired binding and immobilization reactions. Other chromatographic solvents such as high performance liquid chromatography (HPLC) solvents and high performance thin layer chromatography (HPTLC) solvents which favor solubilization of proteins and other reactants and minimize binding to strip materials such as nitrocellulose may also be used.

EXAMPLE 1

According to this example, casein was subjected to an alkaline treatment purification procedure. Two hundred grams of essentially vitamin free casein (Sigma Chemical Co., St. Louis, Mo., catalogue no. C-3400) was mixed with 800 ml of distilled water. One liter of 2 M sodium hydroxide was then added, followed by 4 ml of 30% hydrogen peroxide and the mixture was mixed overnight at room temperature.

The material was filtered through Whatman No. 1 filter paper on a Buchner funnel and approximately 94.6 ml of 100% (glacial) acetic acid was added to the filtrate to bring the pH to 7.5. The mixture was again filtered, as before, and approximately 220 ml of acetic acid was added to the filtrate to bring the pH to about 4.5. The mixture was incubated for 30 minutes during which time a large taffy-like lump fell out of solution. The supernate was centrifuged at 2800 rpm in a small RC5C centrifuge for 30 minutes and the pellet was added to the taffy-like lump which was then washed with deionized water.

The taffy-like material was then stirred and dissolved in one liter of 0.15 M aqueous ammonia solution. (In the event that the casein does not go into solution, concentrated (15 M) ammonium hydroxide solution should be added until the pH reaches 7.5.) The casein was then lyophilized overnight when it was completely dried, having a yield of 136 grams.

EXAMPLE 2

According to this example, a colloidal gold/antibody conjugate was produced for practice of the methods of the present invention, Siliconized glassware (Sigma silicote) was utilized throughout the procedure wherein 200 ml of 0.01% gold chloride ($HAuCl_4.3H_2O$) (Fisher Scientific, G-54-1) was brought to a boil and 2 ml of 1% sodium citrate solution was added and the boiling is continued for 5 minutes until the color of the solution changes from pale yellow to purple to red. A solution of potassium carbonate (0.02M) was added to the suspension in order to adjust the pH to 7.6, followed by addition of goat anti-human IgG (1 mg/ml) (Kirkegaard-Perry, Gaithersburg, Md.) such that approximately 10 µg IgG was added per ml of gold suspension (0.01% gold).

After one minute of incubation at room temperature, 0.1 ml of a solution of 30% bovine serum albumin in water was added to 10 ml of the gold suspension. Aggregated material was removed by centrifugation at 3000 rpm in the SS34 rotor of a Sorval RC5C centrifuge for 10 minutes. The supernate was subjected to an additional centrifugation step at 6000 rpm for one hour. The colloidal gold conjugate in the pellet was resuspended in 2% bovine serum albumin in PBS (0.05 M potassium phosphate buffer, pH 7.4, in 0.9% NaCl), the preferred conditions for liquid storage being at 4° C. The meta-soluble preparation of casein, prepared as in Example 1, was added to give a concentration of 1% immediately before application to the membrane. The conjugate was then stored for prolonged periods in the dry state, with no loss of activity after 6 months storage at 37° C. in the dry state.

EXAMPLE 3

According to this example, sandwich-type immunoassay devices for the detection of rubella antibodies were constructed and used. Microporous nitrocellulose material with a thickness of approximately 0.1 mm and an average pore size of 5 µm was laminated with mylar and adhesive (Monokote, Top Flite Models, Inc., Chicago, Ill.). Strips measuring 1 cm by 3.5 cm were cut by high powered laser and solvent transport lanes and a delaying box were fashioned by laser etching according to the general design of the device of FIG. 4. Rubella antigen (Abbott Laboratories, North Chicago, Ill.) (0.2 µl, 2500 HA titer) was applied to the strips at a third zone where it was immobilized and air dried. Non-specific binding sites on the chromatographic strip materials were then blocked by incubation for 10 minutes at room temperature with a 0.1% solution of LB gelatin in water (Inotech, Wohlen, Switzerland) and the strips were allowed to dry under a stream of air. One µl of gold particle labelled goat anti-human IgG in an anti-aggregation buffer produced according to Example 2 was then applied to a first zone of each strip (adjacent to the delay box) and dried.

Positive and negative serum samples for the rubella antibody were then applied to the second zones between the first and third zones and the first end of the strips were dipped into a chromatographic transport solvent comprising TBS and 1% TRITON X-100 (polyethylene glycol tert-octylphenyl ether). The liquid front was allowed to progress to the second ends of the devices over a period of approximately 2.5 minutes transporting the sample material and the gold labelled goat anti-human IgG to the third zone. Positive sera and the immobilization of the labelled first reagent resulted in the presence of a red spot at the third zone. Strips tested with negative sera did not produce a signal at the third zone.

EXAMPLE 4

In this example a mix and run sandwich-type immunoassay device for the detection of human chorionic gonadotropin (HCG) was constructed and used. The device which is fashioned of the same general design as the device of FIG. 2 produces a signal confirming the presence of a labelled first specific reagent in the sample as a negative control and produces an additional signal indicating the presence of the HCG analyte. Microporous nitrocellulose material with a thickness of approximately 0.1 mm and an average pore size of 5 µm was laminated with mylar and cement (Monokote) according to the methods of Example 3.

At a first zone, the strips were impregnated with a second reagent comprising 0.35 µl of 2 mg/ml anti-HCG polyclonal antibody in buffered saline containing 1% sucrose. At a second zone the strips were impregnated with a third reagent comprising 0.45 µl of a 100 ug/ml goat anti-mouse IgG in Tris buffered saline containing 1% sucrose. The two zones were located approximately 10 mm from the first end of the strip and were arranged such that the second zone was in the form of a minus (−) sign and the first zone was located on two sides of the second zone so that the two zones together form a plus (+) sign.

Anti-HCG antibodies (Abbott Laboratories, North Chicago, Ill.) were incubated with 1 ml of colloidal gold suspension adjusted to pH 6.6 with potassium carbonate according to the method of Example 2 such that approximately 10 µg IgG was added per ml of gold suspension. Indicator solution was then prepared comprising 10 µl of colloidal gold labelled anti-HCG antibody. The gold particle labelled antibodies were added to 10 µl of Tris-buffered saline containing 10% alkaline treated casein according to Example 1 and 1% PEG (M.W. 20,000). The indicator solution was then mixed with 100 µl of a urine sample to which varying amounts of HCG had been added.

The test strip was then contacted at its first end in the mixture of sample and indicator solution and the liquid front was allowed to rise through the zones to the second end of the strip. When the sample solution did not contain any of the HCG antigen the mixture of sample and indicator solution progressed through the strip. Upon contacting the second zone where the goat anti-mouse IgG had been immobilized the labelled anti-HCG antibodies were immobilized by the selective immunological reaction. As no HCG was present in the sample solution there was no specific binding with the second reagent immobilized at the first zone. The colloidal gold labelled reagents thus produced a visually detectable signal in the form of a minus (−) sign indicating operability of the reagents but absence of HCG in the sample.

When the sample solution contained HCG the labelled anti-HCG antibodies selectively bound to the analyte to form a labelled conjugate. The mixture of the sample solution and the indicator solution was transported by chromatographic solvent transport through the first and second zones to the second end. Upon contacting the first zone where polyclonal anti-HCG antibodies had been immobilized the gold labelled antibody/HCG conjugate was immobilized by a specific binding reaction of the HCG antigen with the anti-HCG antibodies. At the same time, the HCG/antibody conjugates and any unconjugated labelled anti-HCG antibodies contacting the second zone were immobilized by contacting the goat anti-mouse IgG antibodies immobilized at that zone. The colloidal gold labelled reagents thus immobilized at both the first and second zones produced a visually detectable signal in the form of a plus (+) sign indicating the presence of HCG in the sample. The sensitivity for HCG of this format was determined to be as low as 25 milli-IU/ml.

EXAMPLE 5

In this example, a mix and run sandwich-type immunoassay for the detection of A-polysaccharide (APS) was prepared and used according to the methods of Example 4. According to this example, nitrocellulose strips were prepared according to Example 4 and were treated with polyclonal anti-APS antibodies which were immobilized at the first zone.

Rabbit polyclonal anti-APS antibodies (Abbott Laboratories, North Chicago, Ill.) were incubated with 1 ml of colloidal gold suspension adjusted to pH 7.2 with potassium carbonate according to the method of Example 2 such that approximately 10 μg of anti-APS antibody was added per ml of gold suspension. An indicator solution was then prepared comprising 10 μl of colloidal gold labelled anti-APS antibodies. The gold particle labelled antibodies were added to 10 μl of Tris-buffered saline containing 10% alkaline treated casein according to Example 1 and 1% PEG. The indicator solution was then mixed with 100 μl of a swab extraction buffer for strep to which varying amounts of APS (Abbott Laboratories, North Chicago, Ill.) had been added.

The test strip was then dipped at its first end in the mixture of a sample and indicator solution and the liquid front was allowed to rise through the first zone to the second end of the strip. APS present in the samples reacted with and was bound to the anti-APS antibodies in the indicator solution to form a conjugate. These conjugates were then immobilized at the first zone by reaction between the APS and the anti-APS polyclonal antibodies immobilized at the zone. The presence of APS in the swab extracted sample was indicated by the development of a purple color as a consequence of the concentration of the colloidal gold particles at the zone. The sensitivity for APS of devices according to this format was determined to be as low as 0.5 ng/ml APS.

EXAMPLE 6

In this example, sandwich-type immunoassay devices for the detection of swine anti-trichina antibodies were produced according to the general procedures of Example 3. Nitrocellulose assay strips were prepared and were treated with partially purified trichina antigen (United States Department of Agriculture) immobilized at a detection zone.

Colloidal selenium particles of various sizes were produced according to the methods of co-owned U.S. Pat. No. 4,954,452. Various volumes (40, 80 and 150 μl aliquots) of concentrated selenium sol were pipetted into individual vials containing 4 ml of water each and the pH of each solution was adjusted to 7.2 by addition of 0.01 M potassium carbonate. To each of the vials was then added 150 μl of goat anti-swine antibody (1 mg/ml concentration) (Kirkegaard-Perry). The solutions were mixed and allowed to incubate for 10 minutes. A 0.5 ml aliquot of a 0.5% solution of alkaline treated casein was added to each solution and mixed well. Three ml aliquots of each selenium conjugate solution were centrifuged in 1 ml portions on a TDx table centrifuge and the pellets were combined for each conjugate after the supernatant was decanted off. The combined pellets of each conjugate were resuspended with a solution of 4% casein in 20 μl of TBS. 0.5 μl aliquots of the selenium particle labelled antibody indicator solutions were then applied to a first zone of each strip (adjacent to the delay box) and dried.

Positive and negative serum samples containing Trichina antibodies were then applied to the second zones of the devices between the first and third zones and the first end of the strips were dipped into a chromatographic transport solvent comprising TBS and 1% TRITON x-100 (polyethylene glycol tert-octylphenyl ether). The liquid front was allowed to progress to the second ends of the devices over a period of approximately 2.5 minutes, transporting the sample material and the selenium labelled anti-swine antibodies to the third zone. All conjugates gave visible positive signals with the conjugate utilizing 80 nm selenium particles providing the best results. All the conjugate solutions were tested against a negative control which indicated no specific binding.

EXAMPLE 7

In this example, a mix and run sandwich-type immunoassay device was constructed and used according to the general procedures of Example 4. Instead of incubating the anti-HCG antibodies with gold particles the antibodies were incubated with colloidal selenium particles produced according to the methods of co-owned U.S. Pat. No. 4,954,452 Selenium particles of varying sizes were tested against varying concentrations of HCG. The conjugate utilizing 80 nm particles gave the best results with a detection limit of 20 mIU/ml. Antibodies labelled with larger or smaller particles gave less sensitive results as shown in Table 1 below. All conjugate solutions were tested against a negative control which indicated no specific binding.

TABLE 1

| Particle Size (nm) | Detection Limit (mIU/ml) |
| --- | --- |
| 11 | 500 |
| 80 | 20 |
| 140 | 50 |
| 193 | 50 |
| 300 | 4000 |

EXAMPLE 8

According to this example, sandwich-type immunoassay devices for the detection of rubella antibodies were constructed and used according to the general procedures of Example 3. Instead of the gold particle labelled goat anti-human IgG, however, alkaline phosphatase labelled goat anti-human IgG (Kirkegaard-Perry) was used to detect the presence of rubella antibodies immobilized at the second zones. One μl of 1 mg/ml of the alkaline phosphatase labelled IgG was diluted in a PBS solution containing 1% alkaline treated casein and was applied to the first zone of each strip and dried. The assay devices could then be constructed, stored for prolonged periods and used in the manner of the gold labelled assay devices of Example 3 with the exception that enzyme substrate and indicator dye reagents must be added to the test strips in order to visualize the assay results.

Numerous modifications and variations in practice of the invention are expected to occur to those skilled in the art upon consideration of the foregoing descriptions of preferred embodiments thereof. The use of colloidal particle labelled reagents in chromatographic assay techniques is of wide applicability and is not limited to the specific examples disclosed. It is thus, well within the skill in the art to practice the present invention according to a wide variety of methods and formats. Consequently, only such limitations should be placed on the invention as appear in the following claims.

What is claimed is:

1. A method for determining the presence or amount an analyte in a test sample, the method comprising the steps:
   a) contacting a chromatographic medium with a test sample, wherein the medium comprises at least two reaction sites;
      a first reaction site comprising a dried colloidal particle labeled specific binding reagent and a chromatographic transport facilitating agent, and a second reaction site comprising an immobilized specific binding agent capable of immobilizing said colloidal particle labeled specific binding reagent;

b) solubilizing said colloidal particle labeled specific binding reagent and said chromatographic transport facilitating agent and chromatographically transporting the test sample and at least a portion of said colloidal particle labeled specific binding reagent from the first reaction site to the second reaction site by capillary interaction of said test sample and said chromatographic medium; and c) detecting said colloidal particle specific binding reagent at said second reaction site to determine the presence or amount of the analyte in the test sample.

2. The method according to claim 1 wherein said chromatographic transport facilitating agent is a meta-soluble protein.

3. The method according to claim 1 wherein said chromatographic transport facilitating agent is casein.

4. The method according to claim 1 wherein said chromatographic transport facilitating agent is polyethylene glycol.

5. The method according to claim 1 wherein said chromatographic transport facilitating agent is gelatin.

6. The method according to claim 1 wherein said chromatographic transport facilitating agent is bovine serum albumin.

7. The method according to claim 1 wherein said chromatographic transport facilitating agent is a detergent.

8. The method according to claim 1 wherein said colloidal particles have a diameter ranging from about 1 nm to about 200 nm.

9. The method according to claim 8 wherein said colloidal particles have a diameter ranging from about 40 nm to about 80 nm.

10. The method according to claim 1 wherein said colloidal particles are colloidal metal particles.

11. The method according to claim 10 wherein said colloidal metal particles are colloidal gold particles.

12. The method according to claim 1 wherein said colloidal particles are non-metal colloidal particles.

13. The method according to claim 12 wherein said colloidal particles are colloidal selenium particles.

* * * * *